US010261092B2

(12) United States Patent
Plocher et al.

(10) Patent No.: US 10,261,092 B2
(45) Date of Patent: Apr. 16, 2019

(54) CROSS-REACTIVE DETERMINANTS AND METHODS FOR THEIR IDENTIFICATION

(71) Applicant: Elanco Tiergesundheit AG, Indianapolis, IN (US)

(72) Inventors: Thomas Plocher, Larchwood, IA (US); Manuel Campos, Alberta (CA); Richard Harland, Mississauga (CA); Todd Johnson, Larchwood, IA (US); Trent Harbison, Larchwood, IA (US); Dan Keil, Spring Hill, KS (US)

(73) Assignee: Elanco Tiergesundheit AG, Greenfield, IN (US)

( * ) Notice: Subject to any disclaimer, the term of this patent is extended or adjusted under 35 U.S.C. 154(b) by 295 days.

(21) Appl. No.: 14/696,904

(22) Filed: Apr. 27, 2015

(65) Prior Publication Data

US 2015/0293118 A1    Oct. 15, 2015

Related U.S. Application Data

(62) Division of application No. 12/934,654, filed as application No. PCT/EP2009/053281 on Mar. 20, 2009, now Pat. No. 9,046,528.

(60) Provisional application No. 61/040,260, filed on Mar. 28, 2008.

(51) Int. Cl.
| | |
|---|---|
| *G01N 33/50* | (2006.01) |
| *G01N 33/68* | (2006.01) |
| *A61K 39/102* | (2006.01) |
| *A61K 39/00* | (2006.01) |

(52) U.S. Cl.
CPC ....... *G01N 33/6854* (2013.01); *A61K 39/102* (2013.01); *G01N 33/5052* (2013.01); *G01N 33/6878* (2013.01); *A61K 2039/552* (2013.01); *G01N 2333/285* (2013.01)

(58) Field of Classification Search
None
See application file for complete search history.

(56) References Cited

U.S. PATENT DOCUMENTS

| | | | |
|---|---|---|---|
| 6,713,071 | B1 | 3/2004 | Ankenbauer et al. |
| 8,911,743 | B2 | 12/2014 | Oliveira |
| 2004/0198954 | A1 | 10/2004 | Ankenbauer et al. |
| 2004/0214272 | A1 | 10/2004 | La Rosa et al. |
| 2009/0131524 | A1 | 5/2009 | Gibson et al. |
| 2011/0014225 | A1 | 1/2011 | Plocher et al. |

FOREIGN PATENT DOCUMENTS

| | | |
|---|---|---|
| EP | 2262828 | 12/2010 |
| WO | 2009/118273 | 10/2009 |
| WO | 2011/056954 | 5/2011 |

OTHER PUBLICATIONS

Sun et al Infection and Immunity, Jan. 2001, 69/1:336-344.*
Topfer et al, Vaccine, 2007, 25:314-326 (available online Aug. 2, 2006).*
Nielsen, Acta Vet. Scand., 1993, 34:193-198.*
Database NCBI GenBank, pyridoxine kinase {Haemophilus parasuis 29755], Database accession ZP_02478801, (Feb. 14, 2008).
Database NCBI GenBank, ABC-type phosphate/phosphonate transport system periplasmic component [Haemophuilus parasuis 29755], Accession ZP_02477404, Feb. 14, 2008.
PCT International Search Report dated Jul. 2009.
PCT Written Opinion of the International Searching Authority dated Jul. 2009.
Gioia et al., J. Bacteriology (2006) 188/20:7257-7266.
Haemophilus parasuis (Glasser's Disease), Iowa State University, (2013),4 pages.
Iowa State University of Science and Technology, Peptides for Vaccines and Diagnosis of Glasser's Disease, May 2013.
Oliveria et al., Vet. Microbiol., (2004), 99:1-12.
Intervet, Porcillis® Glasser for the control of Haemophilus parasuis, Nov. 2004.
Sun et al., "Avidity, potency, and cross-reactivity of monoclonal antibodies to pneumococcal capsular polysaccharide serotype 6B", Infection and Immunity, (Jan. 2001), pp. 336-344, v 69:1.
Beal et al., "Cross-reactive cellular and humoral immune responses to *Salmonella enterica* serovars Typhimurium and Enteritidis are associated with protection to heterologous re-challenge", Veterinary Immunology and Immunopathology, (Nov. 2006), pp. 84-93, v. 114:1-2.
Takahashi et al., "A cross-protection experiment in pigs vaccinated with Haemophilus parasuis serovars 2 and 5 bacterins and evaluation of a bivalent vaccine under laboratory and field conditions". The Journal of Veterinary Medical Science, (May 2001), 487-491, 5.
Database NCBI GenBank, transketolase 2 [Haemophilus parasuls 29755], Database accession ZP-02478744, (Feb. 14, 2008).
Database NCBI GenBank, Holiday Junction DNA helicase B [Haemophilus parasuis 29755], Database accession ZP_02477919, (Feb. 14, 2008).
Database NCBI GenBank, ABC transporter, periplasmic binding protein [Haemophilus parasuls 29755], Database accession ZP_02478157, (Feb. 14, 2008).

* cited by examiner

*Primary Examiner* — Nita M. Minnifield
(74) *Attorney, Agent, or Firm* — David L. Pflugh

(57) ABSTRACT

Compositions and methods for determining immunologically cross-reactive molecules comprising a cross-reactive antigenic determinant are provided, in particular for determining proteins comprising cross-reactive antigenic determinants, in particular for determining proteins that are cross-reactive based on serological screens using sequential immunological challenges to an animal, including determining cross-reactive *H. parasuis* proteins. Also provided are compositions, vaccines, and kits using the molecules for diagnostics and methods for preventing or treating a disease, disorder, condition, or symptoms thereof associated with infectious agents, in particular infectious microorganisms, in particular for preventing or treating a disease, disorder, condition, or symptom thereof associated with *H. parasuis* infection.

5 Claims, 11 Drawing Sheets

Specification includes a Sequence Listing.

CROSS-REACTIVE DETERMINANTS AND METHODS FOR THEIR IDENTIFICATION

CROSS REFERENCE TO RELATED APPLICATIONS

This application is a divisional application of U.S. application Ser. No. 12/934,654, filed Sep. 26, 2010 and issued as U.S. Pat. No. 9,046,528 on Jun. 2, 2015, which is a 371 application of International Application No. PCT/EP2009/053281, filed Mar. 20, 2009, which claims benefit of Provisional Application No. 61/040,260, filed Mar. 28, 2008, each of which is incorporated by reference herein in its entirety.

FIELD OF THE INVENTION

The present invention relates to compositions and methods for determining immunologically cross-reactive molecules comprising a cross-reactive antigenic determinant, in particular for determining proteins comprising cross-reactive antigenic determinants, in particular for determining proteins that are cross-reactive based on serological screens using sequential immunological challenges to an animal, including determining cross-reactive *H. parasuis* proteins. Also provided are compositions, vaccines, and kits using the molecules for diagnostics and methods for preventing or treating a disease, disorder, condition, or symptoms thereof associated with infectious agents, in particular infectious microorganisms, in particular for preventing and treating a disease, disorder, condition, or symptom thereof associated with *H. parasuis* infection.

BACKGROUND OF THE INVENTION

The principle of vaccination is essentially based on two key elements of immunity, namely specificity and memory, Activation and differentiation of B cells in response to most antigens requires various signals that drive B cells to form either antibody secreting plasma cells or memory B cells poised to mediate a more rapid response upon secondary exposure to antigen. Memory cells allow the immune system to mount a much stronger response on the second encounter with antigens. This secondary response is both taster to appear and more effective than the primary response. However, because antibodies by nature are very specific, and in view of the diversity of infectious agents, it has still remained a significant problem to develop antibodies that exhibit cross-reactivity across or within the numerous different types of pathogens.

One example of an infectious agent for which there remains a significant challenge to develop antibodies that exhibit cross-reactivity is *Haemophilus parasuis* (*H. parasuis*), the etiological agent of porcine polyserositis and arthritis (Glasser's disease). *H. parasuis* is a Gram-negative, occasionally-capsulated, non-motile, pleomorphic bacterium isolated from serous exudates of swine affected by serofibrinous pleuritis, pericarditis, peritonitis, arthritis, and meningitis. This organism, which was initially described by Glässer in 1910, was likely isolated for the first time by Schermer and Ehrlich in 1922, though the suspect organism was originally referred to as *Haemophilus suis*. In 1969, however, Biberstein and White showed that the causative agent of Glässers required only nicotinamide adenine dinucleotide (NAD). *Haemophilia suis*, an organism requiring both iron porphyrin and nicotinamide adenine dinucleotide (NAD), was therefore not the insidious character in this disease and the new organism was renamed, by the addition of the prefix "para", to *H. parasuis*.

*H. parasuis* characterization has evolved significantly over the past five decades. Bakos, et al. used a precipitation test to identify four serovars, which be designated A-D (*Nordic Veterinary Medicine,* 4:241-255 (1952)). These four grew to seven in 1986 (*J Clin Microbiol,* 23:1022-1025 (1986)). Kielstein et al., *Zentralbl Veterinarmed B,* 38:315-320 (1991) added six more and, working with Rapp-Gabrielson, *Am J Vet Res,* 53:659-664 (1992), yet another five. Eventually, this classification was refined. All of the serovars, including the few with multiple designations, were characterized based on an immunodiffusion test performed with specific rabbit sera. The result was a list of at least fifteen serovars that have become accepted globally. Unfortunately, a significant number of untypeable isolates also exist. Furthermore, a number of publications have described the serope profiles of *H. parasuis* in specific countries. It has been proposed that in the USA, Germany, Japan, Spain, Canada, and China, serotypes 4 and 5 are quite common. Serotypes 5 and 13 have been reported to be prevalent in Australia and Denmark.

The virulence factors of *H. parasuis* have not been defined. Most associations to virulence are made according to serotype, as some correspond to higher morbidity and mortality rates. Upon intraperitoneal infection, serotypes 1, 5, 10, 12, 13, and 14 have been reported to cause high morbidity and morality rates within 4 day. As such, these strains are considered highly virulent. Three serotypes (i.e., 2, 4, and 15) presented intermediate levels of virulence by causing polyserositis without mortality. The remaining serotypes are considered avirulent as affected swine did not manifest clinical disease.

Attempts have been made to determine specific virulence factors of *H. parasuis*. Being a member of the Pasteurellaceae family, it was thought that some candidates would include capsules, fimbriae, lipopolysaccharides (ITS), and outer membrane proteins (OMPs). At present, however, few correlations can be drawn between these traits in *H. parasuis* and virulence. Encapsulated strains are common in both the nasal cavities of healthy swine and clinically manifesting animals. LPS's importance was somewhat debunked by reports suggesting no significant difference in LPS production between virulent and avirulent serotypes and showing that presentations containing both LPS and OMPs elicited responses to the OMPs exclusively.

OMPs have been shown to generate a strong humoral response and candidates for protective immunogens from this category have been proposed. Two general profiles of OMPs are present and may be associated with virulence. Most virulent serotypes are characterized by the second profile, which is dominated by a 37 kDa protein. Avirulent serotypes show multiple bands, with strong handing between 23-40 kDa, as well as a protein of approximately 68 kDa.

Several other proteins associated with *H. parasuis* infections have been suggested. Two colonization proteins have been reported, designated P2 and P5, which are both immunogenic. P2, surprisingly, appeared to differ depending on serotype virulence. It is dominantly present as a 55 kDa protein in avirulent serotypes and 48 kDa in virulent serotypes. This protein shows homology to *Haemophilus influenzae*'s P2 protein. Others have identified and described the upregulation of the TonB region of *H. parasuis*'s genome. This region contains several genes that respond to iron-depleted environments. Specifically, a transferrin-binding protein was identified and shown to be upregulated when iron is restricted. As iron is sequestered in the host, it has been proposed that such genes may be important for pathogen survival within the host.

Additionally, a 42 kDa major outer membrane protein (MOMP) was detected using a polyclonal antibody directed against the 35 kDa MOMP of *Pasturella multocida*. Analysis of a potentially similar 42 kDa protein of *Haemophilus ducreyi*, a closely related species, characterized the protein as antigenically similar to OmpA. This class of heat-modifiable membrane protein was investigated further through the development of monoclonal antibodies against *H. parasuis* membrane preparations. Two monoclonal antibodies were used in this experiment, one against a 35 kDa OMP and a second against LPS. These monoclonal antibodies were reported to react specifically with the common serotypes and their potential value as diagnostic tools or potential vaccine targets was suggested.

Neuraminidase is another potential virulence factor. More than 90% of field isolates appear to produce neuraminidase. This enzyme is expressed late in the growth phase of *H. parasuis* and is correlated with both the exposure of necessary colonization receptors and the breakdown of mucin within the host.

*H. parasuis* can infect multiple sites of the host. As a result, clinical signs manifest differently based on the site of infection. The four primary forms of infection are Glässer's disease (fibrinous polyserositis), septicaemia (without polyserositis), myositis acuta (masseter muscle), and respiratory disease. Regardless of site of infection or infection type, symptoms of *H. parasuis* infection have been reported to be somewhat general. Increased temperature, apathy, and loss of appetite are commonly reported. Other common clinical symptoms have been reported to include cough, dyspnoea (shortness of breath), weight loss, lameness, lack of coordination, cyanosis, and exhaustion.

*H. parasuis* has become a major issue after specific-pathogen-free (SPF) herds became prevalent. In part due to the evolution of the hog production business, which includes the establishment of specific-pathogen free herds, *H. parasuis* has appeared as an economically significant pathogen. Typically, the infection targets naive animals, those housed with inadequate hygiene, or those fed poorly. Further, insecure transport and the commingling of different-aged pigs have contributed significantly to outbreaks. The combination of the higher concentrations of animals and the relative naivete of the swine population in these protected herds has been reported to have led to an increase in the incidence of *H. parasuis* induced disease. Complicating matters further is the fact that *H. parasuis* exists in several different regionally specific serotypes. It was reported that exposure or vaccination to one serotype did not necessarily protect against infection by others. As such, autogenous vaccine development was proposed as a control against unknown serotype spread. Due in part to such problems and the delay between autogenous bacterin generation and exposure to swine, a need arose for a cross-protective vaccine that could be administered with confidence regardless of regional serotype prevalence.

Treating *H. parasuis* infection with antibiotics has been proposed for immediate application upon the development of clinical signs. Unfortunately, the penetrative nature of the pathogen requires high doses of antibiotics to be effective and is often cost prohibitive.

Control via vaccination has been attempted with both commercial and autogenous vaccines. Diversity of *H. parasuis* serotypes has complicated vaccination regimens, as cross-protection is rare. Combined with the non-typeable strains, this plethora of antigenic profiles made vaccine development difficult.

Protection by vaccination against homologous challenge also has been proposed. A trio of studies suggested that a killed bacterin product could protect against homologous challenge when created with known serotypes and un-typed field isolates. The studies shed light on the use of autogenous vaccines to control outbreaks to reduce mortality rates.

Some had proposed using virulent strains to protect against heterologous challenge from other virulent strains. One study reported a bivalent vaccine containing serotypes 4 and 5 protected against serotypes 13 and 14. Others, however, failed to show cross-protection between serotypes 2 and 5.

Still others have proposed controlled exposure of piglets to low doses of live, virulent *H. parasuis*. However, due in part to damaging co-infections with other pathogens, such as porcine reproductive and respiratory syndrome virus (PRRSV), this approach has not been recommended as a functional control method.

As currently available methods of controlling various disease-causing infections are limited in effectiveness, in part due to the diversity of disease-causing agents such as *H. parasuis*, effective methods and compositions for treatment and prevention are needed, particularly a need to identify proteins that are cross-reactive that can permit the development of effective vaccines, in particular for treatment and prevention of infection by *H. parasuis*.

SUMMARY OF THE INVENTION

In one aspect, the present invention provides a method for determining a molecule comprising a cross-reactive antigenic determinant. The method comprises contacting at least one antibody with a first antigenic determinant and a second antigenic determinant. The at least one antibody is obtained from an animal sequentially exposed to a first immunological challenge elicited by a first immunogenic composition comprising a first antigenic determinant followed by a second immunological challenge elicited by a second immunogenic composition comprising a second antigenic determinant. Binding of the at least one antibody to the first and the second antigenic determinant is indicative of cross-reactivity thereby determining the molecule.

In another aspect, the present invention provides a method for determining a molecule comprising a cross-reactive antigenic determinant, the method comprising:

a) activating a memory B cell in an animal to produce at least one antibody, wherein activating comprises immunologically challenging the animal with the molecule to elicit an immunological response that activates the memory B cell; and b) contacting the at least one antibody with a second molecule, wherein binding of the at least one antibody to the molecule and the second molecule determines the molecule.

In other aspects, the present invention provides an isolated polypeptide. The polypeptide comprises an amino acid sequence selected from the group consisting of:

(SEQ ID NO: 1)
        ELANAI;

(SEQ ID NO: 2)
        TVLAEKQEII;

-continued

ELANAI; (SEQ ID NO: 1)

TVLAEKQEII; (SEQ ID NO: 2)

APAKGSTIENGIAYPIST; (SEQ ID NO: 3)

MKNLISI; (SEQ ID NO: 4)
and

SPSDKTFKISAIPDYNAAEMT, (SEQ ID NO: 5)

The isolated polypeptide further comprises a cross-reactive antigenic determinant present in a protein expressed by at least two serotypes of *H. parasuis*.

In some aspects, the present invention provides an isolated polypeptide comprising an amino acid sequence selected from the group consisting of:

ELANAI; (SEQ ID NO: 1)

TVLAEKQEII; (SEQ ID NO: 2)

APAKGSTIEAGIAYPIST; (SEQ ID NO: 3)

MKNLISI; (SEQ ID NO: 4)
and

SPSDKTFKISAIPDYNAAEMT, (SEQ ID NO: 5)

wherein the isolated polypeptide further comprises a cross-reactive antigenic determinant and is expressed by *H. parasuis* serotype 5.

In one aspect, the present invention provides a vaccine comprising a prophylactically or therapeutically effective amount of an isolated polypeptide, and a pharmaceutical acceptable vehicle, carrier, or excipient. The polypeptide comprises an amino acid sequence selected from the group consisting of:

ELANAI; (SEQ ID NO: 1)

TVLAEKQEII; (SEQ ID NO: 2)

APAKGSTIEAGIAYPIST; (SEQ ID NO: 3)

MKNLISI; (SEQ ID NO: 4)
and

SPSDKTFKISAIPDYNAAEMT, (SEQ ID NO: 5)

The isolated polypeptide further comprises a cross-reactive antigenic determinant present in a protein expressed by at least two serotypes of *H. parasuis*.

In another aspect, the present invention provides a method for treating or preventing a disease, condition, or symptom thereof associated with *H. parasuis* infection of an animal. The method comprises administering an effective amount of a vaccine comprising a prophylactically or therapeutically effective amount of an isolated polypeptide, and a pharmaceutical acceptable vehicle, carrier, or excipient. The polypeptide comprises an amino acid sequence selected from the group consisting of:

ELANAI; (SEQ ID NO: 1)

TVLAEKQEII; (SEQ ID NO: 2)

APAKGSTIEAGIAYPIST; (SEQ ID NO: 3)

MKNLISI; (SEQ ID NO: 4)
and

SPSDKTFISAIPDYNAAEMT, (SEQ ID NO: 5)

The isolated polypeptide further comprises a cross-reactive antigenic determinant present in a protein expressed by at least two serotypes *H. parasuis*.

In other aspects, compositions, methods, and kits for diagnostics are provided in accordance with the present invention.

Advantages and benefits of the present invention will be apparent to one skilled in the art from reading this specification.

Figure 1:
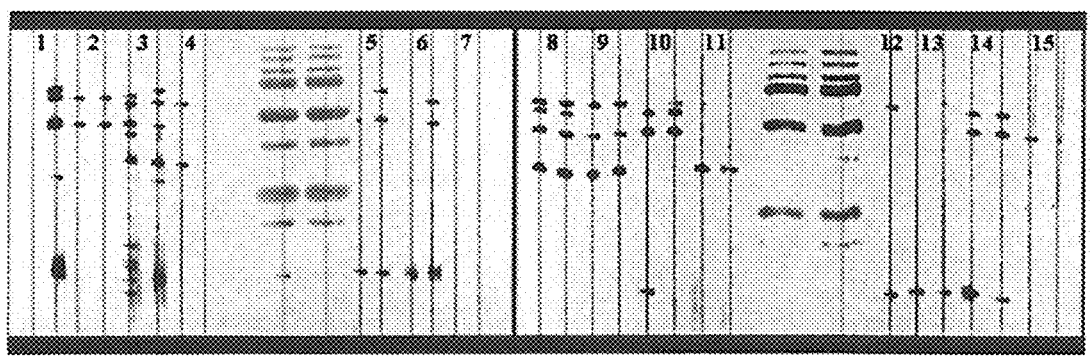
FIG. 1 shows Western Blot for Initial Screening of Bronchial Lymph (BL) Fluids. Samples were run in duplicate with the exception of sample 12. Samples 1-4 and 8-11 are tests against *H. Parasuis* serotype 5 and samples 5-6 and 12-15 are tests against *H. Parasuis* serotype 13. 1: Negative CDCD serum, 2: BL46, 3: BL47, 4: BL50, 5: BL46, 6: BL47, 7: BL50, 8: BL96, 9: BL98, 10: BL99, 11: BL142, 12: BL96, 13: BL98, 14: BL99, 15: BL142.
Figure 2:
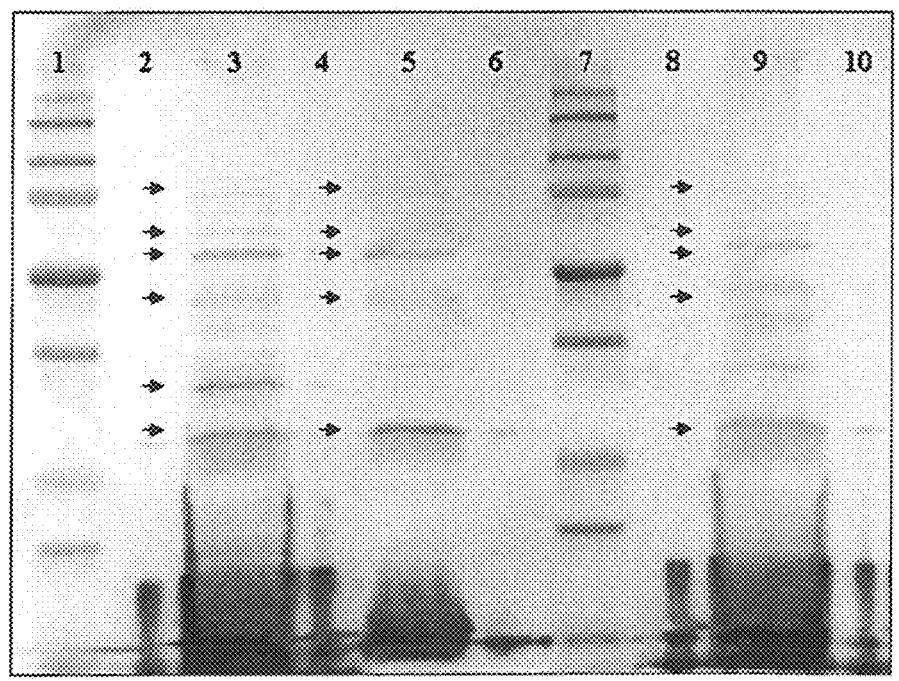
FIG. 2 shows Western Blot of *H. Parasuis* serotypes 5, 13, and 4 with BL47. Lanes 1,7—MW markers (from top: 200, 150, 100, 75, 50, 37, 25, and 20 kDa); Lane 3—*H. Parasuis* serotype 5; Lane 5—*H. Parasuis* serotype 13; Lane 9—*H. Parasuis* serotype 4, Lanes 2, 4, 6, 8, 10—Empty. Arrows indicate prominent bands of interest.

FIG. 3 shows Western Blot and SDS-PAGE of whole cell *H. Parasuis* serotype 5 and Tween-20® Extracted *H. Parasuis* serotype 5. Blot: Lane 1, 5—MW marker (from top: 200, 150, 100, 75, 50, 37, 25, and 20 kDa); Lane 3—whole cell serotype 5; Lane 7—Tween-20® extract of serotype 5, Lane 2, 4, 6—Empty. SDS-PAGE: Lane 1, 5—MW marker: Lane 3—whole cell serotype 5; Lane 7-11—Tween-20® extract of serotype 5; Lane 2, 4, 6. 12—Empty.

FIGS. 4A and 4B shows mass-spectrometry (MALDI MS/MS) of gel-excised band corresponding to ~76 kDa.

FIGS. 4C and 4D show MALDI MS/MS of gel-excised band corresponding to ~63 kDa.

FIGS. 4E and 4F show MALDI MS/MS of gel excised band corresponding to ~56 kDa.

FIGS. 4G and 4H show MALDI MS/MS of gel excised hand corresponding to ~28 kDa.

DETAILED DESCRIPTION

The various aspects and embodiments are provided by virtue of the present invention which comprises the identification of molecules that can provide cross-reactive antibodies that recognize antigenically related molecules, and that can thus be employed in vaccines, diagnostic applications, and methods of treating or preventing a side range of conditions or disease including those associated with infectious agents such as, but not limited to, bacteria, virus, etc.

The novel approach described herein utilizes the host to identify cross-reactive molecules using a staggered immunological challenge model in which a host is sequentially challenged, for example with one serotype of H. parasuis, allowed to recover, then challenged with a different serotype.

I. Definitions

The term "molecule," unless specifically stated otherwise, includes polypeptides and proteins including e.g., glycoproteins and lipoproteins, polysaccharides including e.g., lipopolysaccharides, nucleic acids, and fragments thereof.

The term "immunogen" or "immunogenic" refers to a molecule that induces a specific immune response.

The term "antigenic determinant," as used herein, refers to the primary, secondary, tertiary, or quaternary structure of a molecule (e.g., a polypeptide) recognized by B cells (i.e., B lymphocytes) and the antibodies secreted by B cells.

The term "cross-reactive antigenic determinant," as used herein, refers to the ability of an antigenic determinant present on two or more molecules (e.g., bacterial protein variants) to be bound by the same antibody. Furthermore, it is to be understood that the two or more molecules comprising the antigenic determinant capable of being bound by the same antibody can be: the same molecule or fragments thereof, variants of one another, or different molecules. By way of example with reference to proteins (e.g., bacterial protein variants) comprising an antigenic determinant capable of being bound by the same antibody, the proteins can have the same or a different primary amino acid sequence, however, the proteins each comprise an antigenic determinant (i.e., "cross-reactive") that can be bound by the same antibody.

The term "cross-reactive antibody," as used herein, refers to an antibody capable of binding to a cross-reactive antigenic determinant.

The term "treating," as used herein, refers to ameliorating, improving or remedying a disease, disorder, condition or symptom of a disease, disorder, or condition.

The term "preventing" means to stop or hinder a disease, disorder, condition, or symptom of a disease, disorder, or condition.

II. Determining Cross-Reactivity

In one aspect, the present invention provides a method tor determining a molecule comprising a cross-reactive antigenic determinant. The method comprises contacting at least one antibody with a first antigenic determinant and a second antigenic determinant, wherein the at least one antibody is obtained from an animal sequentially exposed to a first immunological challenge elicited by a first immunogenic composition comprising the first antigenic determinant followed by a second immunological challenge elicited by a second immunogenic composition comprising the second antigenic determinant, wherein binding of the at least one antibody to the first and the second antigenic determinant is indicative of cross-reactivity thereby determining the molecule.

In one embodiment, the first immunogenic composition further comprises a first polypeptide comprising the first antigenic determinant, wherein the second immunogenic composition further comprises a second polypeptide comprising the second antigenic determinant, wherein the first polypeptide is expressed by a first microorganism and the second polypeptide is expressed by a second microorganism, wherein the first and the second microorganism are characterized as being different serotypes of the same species. In another embodiment, the first and the second microorganism is a bacteria. In some embodiments, the bacteria is *H. parasuis*.

Generally, the method Involves two or more sequential immunological challenges to the animal including a recovery time between challenges. Then, at a time subsequent to the last challenge, the at least one antibody is obtained from the animal, e.g, by harvesting the animal's lymph nodes and/or other memory-cell rich tissue comprising the at least one antibody. Without being held to any particular theory, it is believed that by harvesting lymph nodes and/or other memory-cell rich tissue, memory B cells generated to the first challenge can be collected following their activation in response to a subsequent challenge. The activated memory B cells are responsible for the clearing of the first antigenic determinant eliciting the first challenge, and the antibodies they produce in response to a subsequent challenge elicited by the second antigenic determinant can be tested to determine their cross-reactivity with the first and the second antigenic determinant thereby determining their respective cross-reactive molecules.

Suitable animals for use in the method include, but are not limited to, swine (e.g., pigs), bovine, ovine, guinea pigs, rabbits, mice, rats, goats, and horses. In one embodiment, the animal is a cesarean-derived colostrum-deprived animal. In another embodiment, the animal is a pig. In some embodiments, the cesarean-derived colostrum-deprived animal is a cesarean-derived colostrum-deprived pig. In other embodiments, the animal is at least about 1 week of age, illustratively, at least about 1, 2, 3, 4, 5, 6, 7, 8, 9, and 10 weeks of age.

The animal can be exposed to the first and the second immunological challenge in any number of ways so long as memory B cells are generated to the first challenge and are activated upon subsequent challenge of the animal with the second antigenic determinant. Preferably, the antigen is contained in a challenge composition. For example, a first challenge composition comprising the first antigenic determinant and a second challenge composition comprising the second antigenic determinant can be administered to the animal by any suitable route of administration known in the art including, but not limited to, intravenous, intra-arterial, intramuscular, subcutaneous, intradermal, transdermal, oral, and intranasal.

Other manners of exposure to a challenge also within the scope of the invention include vaccinations and natural exposure to an immunogen (e.g., infectious agent). Thus, an immunological challenge also can include a challenge elicited by natural exposure of the animal to an antigenic determinant, such as through exposure of the animal to an infecting agent (e.g bacteria, virus, parasite). Thus, for example, a first immunological challenge can be a challenge elicited by a natural infection of the animal by a strain of bacteria belonging to a first serotype, which is then followed by a second challenge comprising intranasal administration of a second challenge composition having a second serotype (i.e., the second antigenic determinant) of the strain.

A challenge composition comprising an antigen, optionally, can further comprise a buffer and/or further comprise other components that help achieve the desired challenge potency and/or minimize adverse affects to the animal receiving the challenge.

In one embodiment, the first and the second challenge composition comprise a peptone buffer or normal saline. In another embodiment, the first and the second challenge composition comprise a peptone buffer, wherein the first challenge composition further comprises a first bacteria, wherein the second challenge composition comprises a second bacteria, wherein the first and the second bacteria belong to different serotypes of the same species.

In one embodiment, the second challenge is administered to the animal at least about 1 week after the first challenge is administered to the animal, illustratively, about 1 week to about 1 year, about 2 weeks to about 10 months, about 3 weeks to about 8 months, about 1 month to about 6 months, and about 2 months to about 4 months after the first challenge.

Thus, immunological memory provides the basis for the present invention. Accordingly, the method further comprises providing a biological sample from the animal following the second immunological challenge, wherein the biological sample comprises antibody-producing memory cells. The biological sample can be of any suitable type. The biological sample can be from the animal's tissues, organs, blood, lymph, or lymph nodes. The biological sample also can be taken from an infected site or an area of a lesion which may have formed or an area close to an infected site or lesion such as in the lymph nodes. Preferably, the biological sample is obtained by harvesting the animal's lymph nodes and/or other memory-cell rich tissues that provide memory B cells.

Generally, the biological sample is taken from the animal at a time subsequent to the second challenge. Such a time that the sample is taken can vary depending on a number of factors including the animal, the challenge composition, any contemplated steps subsequent to the sample being taken (e.g., subsequent culture conditions), etc., and may be predetermined by routine experimentation. Preferably, the biological sample is taken from the animal following the second challenge at a time when sufficient memory cell activation has occurred. In one embodiment, the biological sample is taken from the animal at about 24 hrs after the second challenge, illustratively, at about 1 day to about 14 days, about 2 days to about 12 days, about 4 days to about 10 days, and about 6 days to about 8 days after the last challenge.

Following removal of the biological sample from the animal, the antibody-producing memory cells that are present in the biological sample can be further processed to obtain the at least one antibody. In one embodiment, following removal of the biological sample from the animal, the antibody-producing memory cells that are present in the biological sample are cultured in vitro. In vitro culturing of the antibody-producing memory cells can be performed with or without prior steps to separate sub-populations of cells. Culturing techniques are known in the art.

The supernatant of the culture can comprise antibodies secreted by the memory cells during the in vitro culturing, therefore, harvesting of the at least one antibody can be performed by harvesting the supernatant from the culture medium. Antibodies produced by the cultured cells also can be released from the cultured cells, for example by lysis of the memory B cells to release the at least one antibody.

In vitro production and/or secretion of the at least one antibody into the culture medium by activated memory cells may be enhanced by adding reagents to the cell culture to promote cell proliferation, and/or enhance antibody production and/or secretion. Such reagents, alone or in combination, include cytokines such as, but not limited to, interleukins, e.g., IL-1, 2, 3, 4, 5, 6, 7 and 8, colony stimulating factors, interferons, and any other factors that may be shown to have an enhancing effect on B cell activation, proliferation, and/or antibody production and/or secretion. For example, cell activation can include adding an activating agent to the culture medium including, but not limited to, mitogens and factors produced by leukocytes, or their synthetic equivalents or combinations thereof. Optionally, antimicrobial agents are included in the culture medium.

The cell culture supernatant comprising the at least one antibody can be used directly to determine binding of the at least one antibody to the first and the second antigenic determinant. In other words, the at least one antibody may be utilized simply in the form of the supernatant harvested from the culture medium.

In other embodiments, the biological sample can be harvested from the animal and the B-lymphocytes contained therein immortalized and/or cloned. Fusion partners are known in the art, which are capable of immortalizing B-lymphocytes. The methods employed for the fusion include combining the B-lymphocytes with a fusion partner in the presence of a fusogen, e.g., a non-ionic detergent, for sufficient time for fusion to occur, followed by selection of the resulting hybridomas via the markers present in the fusion partner. The cells can then be subjected to limiting dilution to provide for clones free of contaminating cells, thereby providing for a homogeneous antibody composition. The hybridomas can then be proliferated in culture or introduced into a host animal, e.g., a mouse or a rat, to produce antibody-rich ascites fluid.

If desired, the at least one antibody can be subjected to purification and/or fractionation schemes. For example, techniques can be utilized such as those used to purify immunoglobulins from serum or plasma, e.g. absorption, precipitation with ammonium sulphate, fractionation with caprylic acid, ion exchange chromatography, or by binding and elution from immobilized protein G or protein A. Also, depending on the particular set-up or application, the at least one antibody also can be coupled to a suitable support, e.g., an affinity chromatography support.

Thus, for example, a solution comprising the at least one antibody also may contain at least one unwanted non-specific antibody, which may be undesirable during the step of contacting the at least one antibody with the first antigenic determinant and the second antigenic determinant. Thus, if desired, the unwanted antibody can be removed from the solution by absorption of the solution comprising the at least one antibody with various reagents including, e.g., egg yolk, tissue powder, suspensions of microorganisms, etc. Pre-immune serum collected from the animal also can be used for absorption. Illustratively, by way of another example, a solution comprising the at least one antibody produced in response to a challenge with one species of bacteria can be incubated with, for example a detergent-extracted bacterial cell suspension of another species, then centrifuging and collecting the supernate comprising the at least one antibody. Absorption can be preformed more than once to minimize non-specific binding due to irrelevant antibodies.

In accordance with the present invention, the method for determining a molecule comprising a cross-reactive antigenic determinant comprises contacting at least one antibody with a first antigenic determinant and a second antigenic determinant. Binding of the at least one antibody to the first and the second antigenic determinant determines the molecule. Contacting can be performed utilizing a technique, or combination of techniques, known in the art. In one embodiment, the method further comprises determining whether or not the at least one antibody binds to the first antigenic determinant and the second antigenic determinant. Exemplary techniques that can be utilized, alone or in combination, include, without limitation, Western blotting, immunoprecipitation, radioimmunoassay, enzyme-linked immunoassay (ELISA), and immunofluorescent assay. Such techniques are particularly preferred where the molecule comprising the antigenic determinant is a protein. In one embodiment, contacting comprises utilizing a Western blot technique to determine binding of the at least one antibody to the first antigenic determinant and the second antigenic determinant, wherein a first and a second protein comprise the first and the second antigenic determinant, respectively.

For example, wherein the molecule to be determined is a protein, a first composition comprising a first protein having the first antigenic determinant and a second composition comprising a second protein having the second antigenic determinant may each be separately mixed with a standard buffer solution and subjected to sodium dodecyl sulfate-polyacrylamide gel electrophoresis (SDS/PAGE), then transferred to nitro-cellulose, nylon, or other membranes prior to contacting the at least one antibody with the first antigenic determinant and the second antigenic determinant. Binding of the at least one antibody to the first antigenic determinant and the second antigenic determinant can then be visualized, for example by adding a secondary antibody, which can be labeled and selected according to the source (i.e., the animal) of the at least one antibody. Then, comparative analysis of detectable bands corresponding to the first and the second protein can be performed to detect binding of the at least one antibody to the first antigenic determinant and the second antigenic determinant, wherein binding of the at least one antibody to the first antigenic determinant and the second antigenic determinant indicates that the at least one antibody is cross-reactive with the first and the second antigenic determinant. Accordingly, the first and the second antigenic determinants are cross-reactive thereby determining the molecules the proteins), which can be further characterized utilizing techniques known in the art.

By way of example, where the cross-reactive antigenic determinant is created by a protein, a number of techniques are known in the art for further characterizing the determined protein comprising the cross-reactive antigenic determinant. For example, following SDS/PAGE or gel transfer to a membrane, a region of the gel or the membrane corresponding to the protein can be excised or eluted from the gel or membrane, and at least partially purified for further analysis using known techniques including mass spectroscopy and N-terminal amino acid sequencing (e.g., Edman degradation). Furthermore, amino acid sequence information can be compared to any known amino acid sequences by homology comparison) to determine and/or further characterize the identity of the protein. Furthermore, amino acid sequence information can be utilized to deduce a corresponding nucleic acid sequence information, which can provide, among other things, primers and probes for specific nucleic acid amplification and/or cloning purposes. Thus, in other embodiments, the method further comprises determining the amino acid sequence of at least a portion of the molecule, wherein the molecule is a protein.

Accordingly, in some embodiments, the present invention provides a method for determining a protein comprising a cross-reactive antigenic determinant. The method comprises contacting at least one antibody with a first antigenic determinant and a second antigenic determinant, wherein the at least one antibody is obtained from an animal sequentially exposed to a first immunological challenge elicited by a first immunogenic composition comprising the first antigenic determinant followed by a second immunological challenge elicited by a second immunogenic composition comprising the second antigenic determinant, wherein binding of the at least one antibody to the first and the second antigenic determinant is indicative of cross-reactivity thereby determining the protein. Contacting is as described above.

In one embodiment, the protein is expressed by *H. parasuis*. In another embodiment, the first immunogenic composition further comprises *H. parasuis* bacteria from a first serotype, wherein the second immunogenic composition further comprises *H. parasuis* from a second serotype. In some embodiments, the first serotype is *H. parasuis* serotype 5 and the second serotype is *H. parasuis* serotype 13.

Accordingly, in other embodiments, the present invention provides a method for determining a molecule comprising a cross-reactive antigenic determinant, the method comprising:

a) activating a memory B cell in an animal to produce at least one antibody, wherein activating comprises immunologically challenging the animal with a second molecule to elicit an immunological response that activates the memory B cell; and b) contacting the at least one antibody with the molecule and the second molecule, wherein binding of the at least one antibody to the molecule and the second molecule determines the molecule.

III. Isolated Molecule

In other aspects, the present invention provides an isolated molecule, or a fragment thereof, comprising a cross-reactive antigenic determinant. In one embodiment, the isolated molecule is a protein. In another embodiment, the cross-reactive antigenic determinant is present in a protein expressed in at least two serotypes of *H. parasuis*.

In one embodiment, the present invention provides an isolated polypeptide comprising an amino acid sequence selected from the group consisting of:

```
                                    (SEQ ID NO: 1)
    ELANAI;

(SEQ ID NO: 2)
    TVLAEKQEII;

(SEQ ID NO: 3)
    APAKGSTIEAGIAYPIST;

(SEQ ID NO: 4)
    MKNLISI;
    and (SEQ ID NO: 5)
    SPSDKTFKISAIPDYNAAEMT,
``` wherein the isolated polypeptide further comprises a cross-reactive antigenic determinant present in a protein expressed by at least two serotypes of *H. parasuis*.

In another embodiment, the present invention provides an isolated polypeptide comprising an amino acid sequence selected from the group consisting of:

```
                                    (SEQ ID NO: 1)
    ELANAI;

(SEQ ID NO: 2)
    TVLAEKQEII;

(SEQ ID NO: 3)
    APAKGSTIEAGIAYPIST;
```

-continued

MKNLISI; (SEQ ID NO: 4)
and

SPSDKTEKISAIPDYNAAEMT, (SEQ ID NO: 5)

wherein the isolated polypeptide further comprises a cross-reactive antigenic determinant and is expressed by *H. parasuis* serotype 5.

Comparison of the amino acid sequences of SEQ ID NOs: 1-5 with various segments of *H. parasuis* amino acid sequences submitted to GEN BANK reveals at least the following homologies: SEQ ID NO:1 & Accession No.: ZP_02478744: SEQ ID NO: 2 & Accession No.: ZP_02477919: SEQ ID NO:3 & Accession No.: ZP_02478157; SEQ ID NO:4 & Accession No.: ZP_012478801; and SEQ ID NO:5 & Accession No.: ZP_02477404. Accession Nos.: ZP_02478744, ZP_02477919. ZP_02478157, ZP_02478801, and ZP_02477404 are incorporated herein by reference in their entirety.

IV. Compositions, Vaccines, Diagnostics, and Kits

In various other aspects of the present invention there is provided methods, compositions, and kits based on the determined molecule comprising the cross-reactive antigenic determinant. Preferably, the determined molecule is a protein expressed by a disease-causing pathogen. The disease-causing pathogen is preferably a bacteria, preferably, *H. parasuis*, however, the invention is not restricted thereto and the description following is merely illustrated by reference to *H. parasuis* and the *H. parasuis* proteins and polypeptides of the present invention.

Vaccines for Active Immunization

In one aspect, the present invention provides vaccines for active immunization designed to treat or protect against *H. Parasuis* infections, and these vaccines can be prepared from the *H. parasuis* protein, or a fragment thereof, comprising the cross-reactive antigenic determinant as set forth above using conventional vaccine preparation methods well known in this field. Typically, an immunogenic amount of the protein, or a fragment thereof, comprising the cross-reactive antigenic determinant is combined with a suitable pharmaceutically acceptable vehicle, carrier or excipient, and an amount of this vaccine effective to immunize a human or animal may be administered as appropriate. By immunogenic, amount it would be understood by one of ordinary skill in this art that this refers to an amount of the protein, or a fragment thereof, comprising the cross-reactive antigenic determinant that is sufficient to raise an immunogenic response in the human or animal.

The desired polypeptides comprising the cross-reactive antigenic determinant which serve as the active ingredients of the vaccines of the invention can be prepared, depending on their size, by any one of a number of approaches known in the art.

For example, if the desired polypeptide sequence is relatively short, e.g., that corresponding to the amino acid sequence consisting essentially of the cross-reactive antigenic determinant, chemical synthesis, using methods now standard in the art, is feasible. In a typical procedure, the C-terminal amino acid can be bound to a solid support, and reacted with the next amino acid in sequence which has been protected at the amino group to prevent self-condensation. After the initial coupling, the $NH_2$ protecting group can be removed, and the coupling process repeated with the amino acid next in order.

Or, for example, the polypeptides of the present invention can be prepared by purification of the native protein from, for example fermentor cultures, followed by generation of the desired fragment by various techniques, and purification of the desired fragment. Recombinant DNA methodology provides another way of synthesizing the desired peptides. The DNA coding sequence (e.g., cDNA, genomic digest) for the desired peptide or protein can be ligated into an expression vector suitable for transforming a recipient strain to express the gene and produce the polypeptide.

Whether derived from a genomic or cDNA library, or by oligonucleotide synthesis using chemical methods, the coding sequence can be placed under the control of promoter sequences compatible with bacterial hosts in plasmids containing convenient restriction sites for insertion of the desired coding sequence. The resulting expression vectors can be transformed into suitable bacterial hosts using method known in the art. Successful transformants may produce the desired polypeptide fragments at higher levels than those found in recombinant or native strains. Alternatively, these peptides can be produced in non-bacterial recombinant hosts using appropriate control sequences, vectors and transformation techniques.

Where the peptide sequences comprising the cross-reactive antigenic determinant are determined to be too small to be immunogenic, they can be linked to carrier substances in order to confer an immunogenic property to them. Any method of creating such linkages known in the art can be used. For example, there are a large number of heterobifunctional agents which generate a disulfide link at one functional group end and a peptide link at the other, and these have been used extensively. The most popular of these is N-succidimidyl-3-(2-pyridyldithio) proprionate (SPDP). This reagent creates a disulfide linkage between itself and a cysteine residue in one protein and an amide linkage through the amino on a lysine, or other free amino group in the other. A variety of such disulfide/amide forming agents are known. Other bifunctional coupling agents form a thioether rather than a disulfide linkage. Many of these thioether forming agents are commercially available and include reactive esters of 6-maleimidocaproic acid, 2 bromoacetic acid, 2-iodoacetic acid, 4-(N-maleimido-methyl) cyclohexane-1-carboxylic acid and the like. The carboxyl groups can be activated by combining them with succinimide or 1-hydroxy-2-nitro-4-sulfonic acid, sodium salt. If the peptide contains no convenient cysteine, an additional cysteine residue at either terminus can be added when the peptide is prepared. As typically only shorter peptides require conjugation to carrier, these residues can be included conveniently during chemical synthesis.

Preparation of vaccines which contain peptide sequences as active ingredients are well understood in the art. Typically, such vaccines are prepared as injectables, either as liquid solutions or suspensions; solid forms suitable for solution or suspension in liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccine.

The vaccines are conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides; such suppositories may be formed from mixtures containing the active ingredient in the range of 0.5% to 10%, preferably 1-2%. Oral formulations include such normally employed excipients as, for example, pharmaceutical grades of manitol, lactose, starch, magnesium sterate, sodium saccharrine cellulose, magnesium carbonate and the like. These compositions take the form of solutions, suspensions, tablets, pills, capsules, sustained release formulations or powders and contain 10%-95% of active ingredient, preferably 25-70%.

The amino acid sequences of the invention include their pharmaceutically acceptable salts, including the acid addition salts (formed with the free amino groups of the peptide) and which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines can be administered in a manner compatible with the dosage formulation, and in such amount as will be prophylactically or therapeutically effective and immunogenic. The quantity to be administered can depend on the subject to be treated, capacity of the subject's immune system to synthesize antibodies, and the degree of protection desired. Precise amounts of active ingredient required to be administered can depend on the judgment of the care-giver/practitioner. Suitable dosage ranges for subcutaneous or muscular injection can be about 1 µg to about 10 mg active ingredient per subject, for example. For oral, rectal suppository, urethral or vaginal preparation, dosages can range, illustratively, from about 10 µg to about 100 mg. Suitable regimes for initial administration and booster shots are also variable, but are typified by an initial administration followed in about one to about two week intervals by a subsequent injection or other administration.

Antibodies

In another aspect, the present invention provides isolated antibodies that can be generated from a protein, or a fragment thereof, comprising the cross-reactive antigenic determinant so as to be able to recognize the cross-reactive antigenic determinant, wherein the protein is expressed by *H. parasuis*. These antibodies can be either monoclonal or polyclonal. If polyclonal antibodies are desired, these may be generated in any of a number of conventional ways known in the art. Typically, the protein, or a fragment thereof, comprising the cross-reactive antigenic determinant can be injected into a suitable host animal, e.g., a mouse or rabbit, and after a suitable time period, antibodies may be isolated and recovered from the host animal. With regard to monoclonal antibodies, in accordance with the present invention, these may be produced in any number of ways including, e.g., by the well known method of Kohler and Milstein, Nature 256:495497 (1975), or such as those methods disclosed in U.S. Pat. Nos. 6,331,415, 5,981,216, 5,807,715, and 4,816,567, which are incorporated herein by reference for their teaching of monoclonal antibodies. Such methods are known in the art and include preparing chimeric, humanized, and human monoclonal antibodies. Monoclonal antibodies also can be prepared from a single chain, such as the light or heavy chains, and in addition also can be prepared from active fragments of an antibody which retain the binding characteristics (e.g., cross-reactivity, specificity, and/or affinity) of the whole antibody. By active fragments is meant an antibody fragment which has the same binding specificity as a complete antibody which binds to the particular cross-reactive antigenic determinant from the different serotypes of *H. parasuis*, and the term "antibody" as used herein is meant to include said fragments. Additionally, antisera prepared using monoclonal polyclonal antibodies in accordance with the invention are also contemplated and may be prepared in a number of suitable ways as would be recognized by one skilled in the art.

Although production of antibodies using recombinant forms of the protein, or a fragment thereof, comprising the cross-reactive antigenic determinant is preferred, antibodies can be generated from natural isolated and purified versions of the protein, or a fragment thereof, comprising the cross-reactive antigenic determinant, and monoclonal or polyclonal antibodies can be generated using the protein, or a fragment thereof, comprising the cross-reactive antigenic determinant in the same manner as described above to obtain such antibodies.

Passive Immunization

In addition to active vaccines wherein antibodies are generated in the patient by virtue of administration of an immunogenic amount of the protein, or a fragment thereof, comprising the cross-reactive antigenic determinant, the isolated antibodies of the present invention, or active fragments thereof; can also be utilized in the development of pharmaceutical compositions and/or vaccines for passive immunization against *H. parasuis* infections.

One skilled in the art will recognize that the antibodies of the present invention (i.e., antibodies able to recognize the cross-reactive antigenic determinant) can also be formed into suitable pharmaceutical compositions for administration to a human or animal in order to treat or prevent an infection caused by *H. parasuis* bacteria. Pharmaceutical compositions containing the antibodies of the present invention, or effective fragments thereof, may be formulated in combination with any suitable pharmaceutical vehicle, excipient or carrier that would commonly be used in this art, including saline, dextrose, water, glycerol, ethanol, other therapeutic compounds, and combinations thereof. As one skilled in this art would recognize, the particular vehicle, excipient or carrier used will vary depending on the intended recipient and the recipient's condition, and a variety of modes of administration would be suitable for the compositions of the invention, as would be recognized by one of ordinary skill in this art. Suitable methods of administering a pharmaceutical composition include, but are not limited to, topical, oral, anal, vaginal, intravenous, intraperitoneal, intramuscular, subcutaneous, intranasal and intradermal administration.

For topical administration, the composition can be formulated in the form of an ointment, cream, gel, lotion, drops (such as eye drops and ear drops), or solution (such as mouthwash). Wound or surgical dressings, sutures and aerosols may be impregnated with the composition. The composition may contain conventional additives, such as preservatives, solvents to promote penetration, and emollients. Topical formulations may also contain conventional carriers such as cream or ointment bases, ethanol, or oleyl alcohol.

The antibody compositions of the present invention can also be administered with a suitable adjuvant in an amount effective to enhance the immunogenic response. For example, suitable adjuvants may include alum (aluminum phosphate or aluminum hydroxide), which is used widely in humans, and other adjuvants such as saponin and its purified component Quil A, Freund's complete adjuvant, RIBBI adjuvant, and other adjuvants used in research and veterinary applications. Examples of other chemically defined preparations include muramyl dipeptide, monophosphoryl lipid A, phospholipid conjugates, encapsulation of the conjugate within a proteoliposome, and encapsulation of the protein in lipid vesicles.

The antibody compositions of the present invention which recognize the cross-reactive antigenic determinant as set forth above will be useful in methods of preventing or treating H. Parasuis infection. In one embodiment, the present invention provides a method for preventing or treating a H. Parasuis infection, the method comprising administering an effective amount of an antibody to the cross-reactive antigenic determinant as set forth herein so as to treat or prevent H. Parasuis infection.

Generally, the preferred dose for administration of an antibody composition in accordance with the present invention is that amount that will be effective in preventing of treating H. Parasuis infection, and one would readily recognize that this amount can vary depending on the nature of the infection and the condition of a subject. An "effective amount" of antibody or pharmaceutical agent to be used in accordance with the invention is intended to mean a nontoxic but sufficient amount of the agent, such that the desired prophylactic or therapeutic effect is produced. The exact amount of the antibody or a particular agent that is required will vary from subject to subject, depending on the species, age, and general condition of the subject, the severity of the condition being treated, the particular carrier or adjuvant being used and its mode of administration, and the like. Accordingly, the "effective amount" of any particular antibody composition will vary based on the particular circumstances, and an appropriate effective amount may be determined in each case of application by one of ordinary skill in the art using routine experimentation. The dose can be adjusted to suit the individual subject to whom the composition is administered and will vary with age, weight and metabolism of the individual. The compositions can also contain stabilizers or pharmaceutically acceptable preservatives.

Accordingly, the antibodies of the present invention will thus provide methods for treating or preventing H. Parasuis infection in a human or animal when an effective amount of the antibody composition is administered to the human or the animal, wherein the effective amount is sufficient to either prevent or treat infection by the bacteria. As would be recognized by one of ordinary skill in this art, the level of antibody titer needed to be effective in treating or preventing infection will vary depending on the nature and condition of the subject, and/or the severity of any preexisting infection.

Furthermore, the antibodies of the present invention can be modified to be less immunogenic when administered. By way of example with reference to a human recipient of the antibody, the antibody may be "humanized" by transplanting the complimentarity determining regions of the hybridoma-derived antibody into a human monoclonal antibody or "veneered" by changing the surface exposed murine framework residues in the immunoglobulin variable regions to mimic a homologous human framework counterpart. Even further, when so desired, the monoclonal antibodies of the present invention may be administered in conjunction with a suitable antibiotic to further enhance the ability of the present compositions to fight bacterial infections as necessary.

Thus, in accordance with the present invention, the protein, or a fragment thereof, comprising the cross-reactive antigenic determinant can be utilized as active vaccines, and the antibodies of the invention may be used as passive vaccines useful in providing suitable antibodies to treat or prevent a H. parasuis infection. As would be recognized by one skilled in the art, a vaccine may be packaged for administration in a number of suitable ways, such as by parenteral (e.g., intramuscular, intradermal or subcutaneous) administration or nasopharyngeal (e.g., intranasal) administration. The vaccine can be lyophilized for resuspension at the time of administration or in solution.

Diagnostics

In other aspects, the antibodies of the invention can also be used for the specific detection of H. Parasuis proteins, or as research tools. The above described antibodies may be labeled directly with a detectable label for identification and quantification of H. Parasuis bacteria. Labels for use in immunoassays are known to those skilled in the art and include enzymes, radioisotopes (e.g., $^{32}P$, $^{3}H$, $^{34}C$, $^{35}S$, $^{325}I$), and fluorescent (fluorescein and derivatives, phycoerythrin, allo-phycocyanin, phycocyanin, rhodamine, and TEXAS RED® fluorochrome), luminescent (e.g., firefly luciferin) and chromogenic substances, including colored particles such as colloidal gold or latex beads. Suitable immunoassays include enzyme linked immunosorbent assays (ELISA). If desired, the antibody may be labeled indirectly by reaction with labeled substances that have an affinity for immunoglobulin. The antibody may be conjugated with a second substance and detected with a labeled third substance having an affinity for the second substance conjugated to the antibody. For example, the antibody may be conjugated to biotin and the antibody-biotin conjugate detected using labeled avidin or streptavidin. The antibody also can be conjugated to a hapten and the antibody-hapten conjugate detected using labeled anti-hapten antibody. These and other methods of labeling antibodies and assay conjugates are well known to those skilled in the art. Detection of a label can be performed byvarious methods including scintillation counting, gamma ray spectrometry, autoradiography, and fluorescence detecting.

Accordingly, when used with suitable labels or other appropriate detectable biomolecule or chemicals, the antibodies described herein are useful for purposes such as in vivo and in vitro diagnosis of H. parasuis infections or detection of H. parasuis bacteria.

Kits

In another aspect, the present invention provides a kit for isolating and determining H. parasuis bacteria and infection. In one embodiment, the kit comprises the isolated cross-reactive antibodies of the present invention in a suitable form, such as lyophilized in a single vessel which can be activated by addition of an aqueous sample suspected of containing the H. parasuis bacteria. Such a kit will typically include a suitable container for housing the antibodies in a suitable form along with a suitable immunodetection reagent. Generally, these kits can contain an antibody in accordance with the present invention and instructions to determine binding of that antibody when a sample from a subject is introduced to the antibody. For example, a suitable immunodetection reagent may comprise an appropriate detectable signal or label, such as a biotin or enzyme that produces a detectable color, etc., which may be linked to the antibody or utilized in other suitable ways so as to provide a detectable result when the antibody binds to the antigen. In another embodiment, the kit comprises a *H. parasuis* protein, or a fragment thereof, comprising a cross-reactive antigenic determinant.

The following examples are provided for illustration only.

EXAMPLES

Example 1

Sequential Challenge

All experimental animals were subject to the procedures set forth by the revised Public Health Service Policy on Humane Care and Use of Laboratory Animals, the Provision of the Animal Welfare Act, and other applicable laws and regulations.

The challenge composition was prepared as follows: a sterile cotton swab was dipped in thawed *H. parasuis* stock at approximately $5 \times 10^8$ Colony forming units (CFU)/ml and gently swabbed to cover the surface of a chocolate agar plate. The culture was incubated at 37° C. for 48 h in an atmosphere with 5% $CO_2$. Three ml of peptone buffer was then used to wash the plate, using a cell scraper and passed through cheesecloth to remove any agar debris. Captured fluid was then normalized to 1 OD with peptone buffer. This level was reached at approximately a 1:11 dilution. The material was stored at 4° C. for approximately 1 h before use.

Eighteen colostrum-deprived, cesarean-derived (CDCD) pigs at 5 weeks of age were obtained from Struve Labs, Inc. Animals were randomly placed into one of three groups: 9 pigs were placed into the experimental group, 4 pigs into the control group, and 5 pigs into the sentinel group (Table 1). All animals were given intranasal canulas to provide direct access to the upper respiratory system and housed in controlled-access rooms according to group.

TABLE 1

Animal Grouping and Challenge

| Experimental Group | *H. Parasuis* Serotype 5 Challenge | *H. Parasuis* Serotype 5 Challenge |
|---|---|---|
| Experimental (9 animals) | X | X |
| Control (4 animals) | | |
| Sentinel (5 animals) | | X |

At 7 weeks of age, animals in the experimental group were challenged intranasally with 1 ml of serotype 5 diluted to a 0.001 optical density (OD) at 530 nm in peptone buffer. Sentinel and control pigs were challenged with peptone buffer. After challenge, pigs were allowed to recover. Broad-spectrum antibiotics were administered as needed.

Nine weeks after the first challenge, animals in the experimental and sentinel groups were challenged intranasally with 1 ml of serotype 13 diluted to a 0.001 OD at 530 nm in peptone buffer.

Three randomly selected animals from each group were necropsied 24 hrs after the second challenge. Respiratory and lymph tissues were harvested from these animals, macerated with a sterile scalpel, and placed in 24-well plates containing cell culture media with antibacterial agents to allow activated cells to proliferate. This media supernatant was used for further testing. Remaining animals were observed for 2 more weeks and necropsied.

Example 2

SDS/PAGE and Western Blot

One ml of frozen *H. parasuis* stock at $5 \times 10^8$ CFU/ml was spread-plated onto chocolate agar plates. The culture was incubated at 37° C. for 48 h in an atmosphere with 5% $CO_2$. Four ml of phosphate buffered saline (PBS) was then used to wash the plate, using pipette-induced flow to suspend the cells. Re-suspended cells were stored at 4° C. and used within 1 week. Two ml of the suspension was centrifuged (9,000 g, 1 hr) and pelleted cells were resuspended in 200 µl of PBS, washed twice with PBS, and disrupted by passage through an 18-gauge needle. The washed cell suspension was mixed 1:1 with PBS containing 2% TWEEN® 20 nonionic detergent and the incubated on a test tube rotator for 90 min at 37° C. After incubation, the cells were removed by centrifugation (48,000 g, 1 hr). The culture supernatant was kept and stored at 4° C. and used within 1 week.

Figure 3:
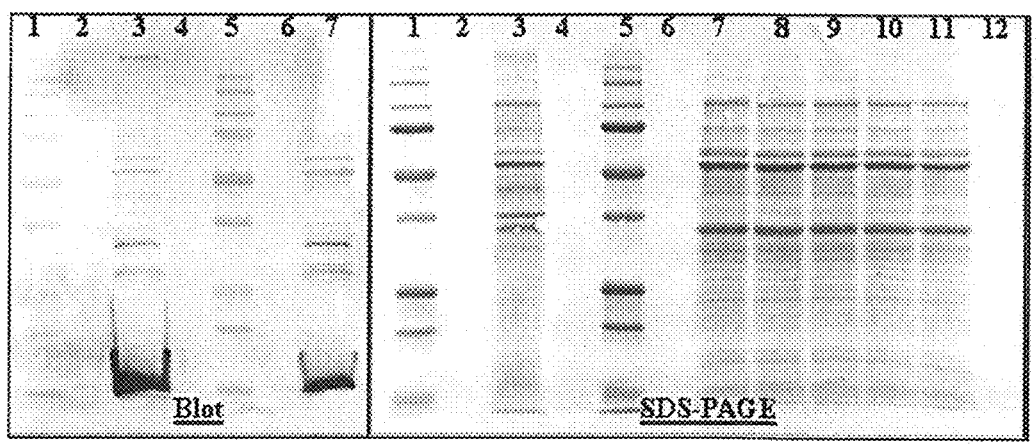
Figure 4A:
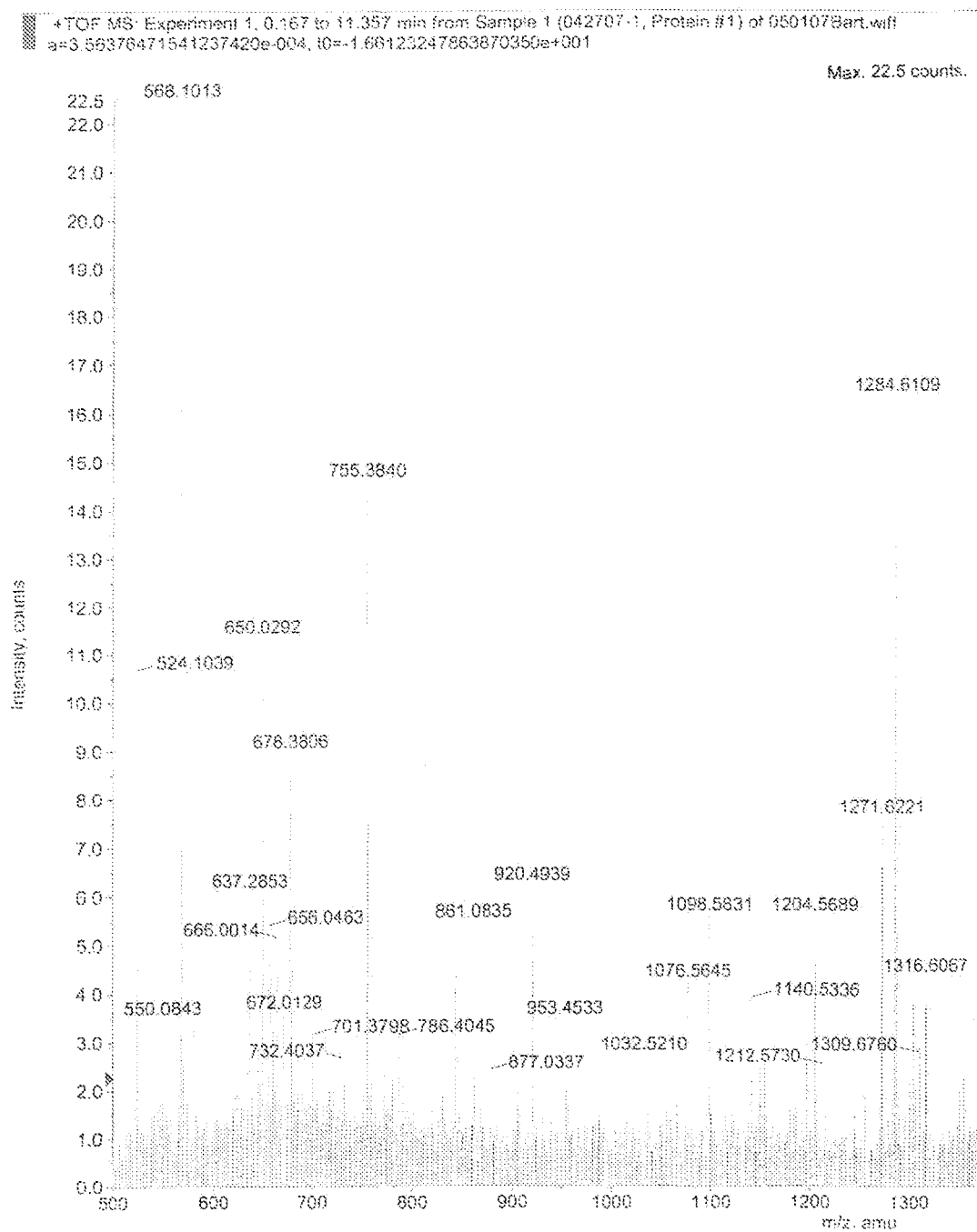
Figure 4B:
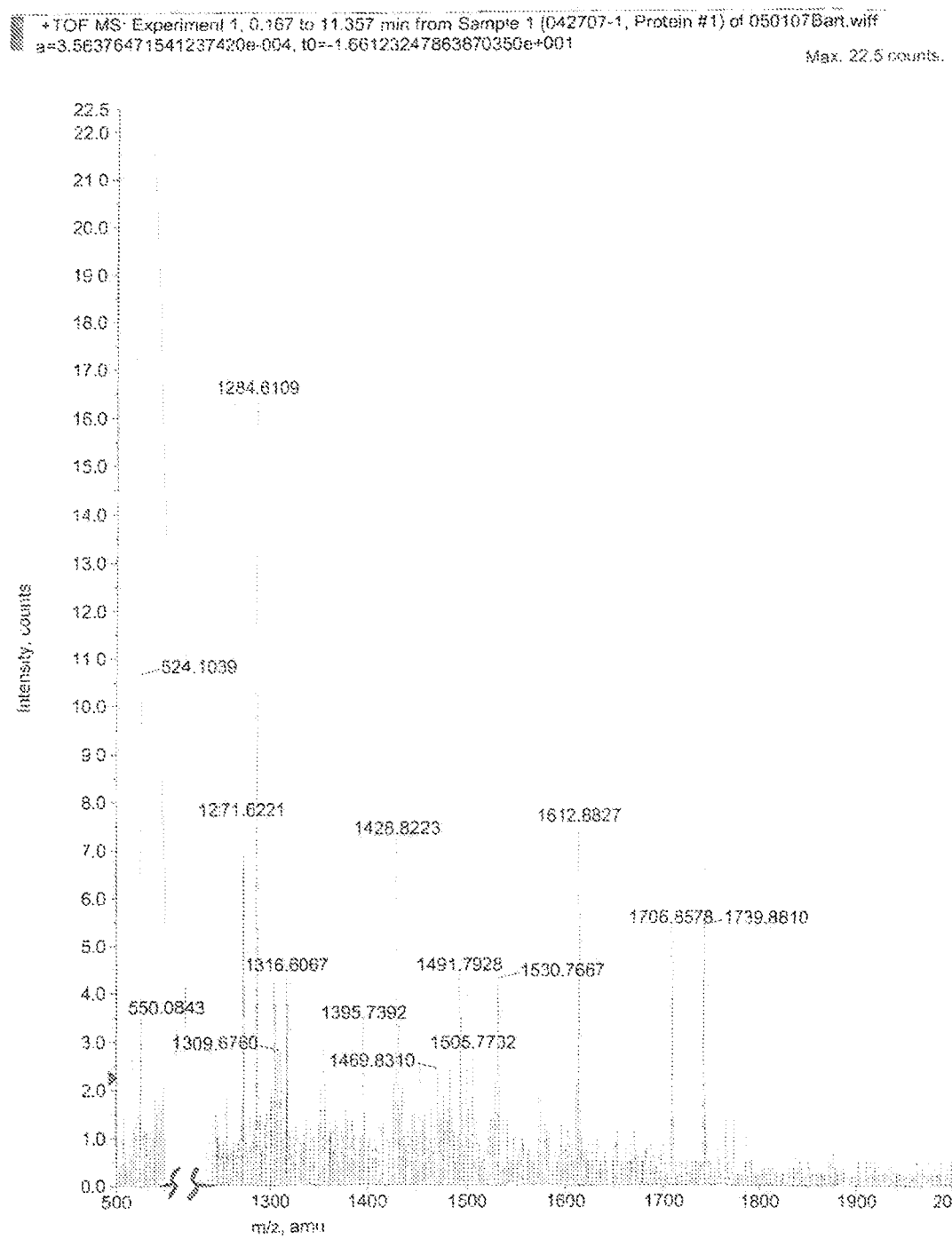
Figure 4C:
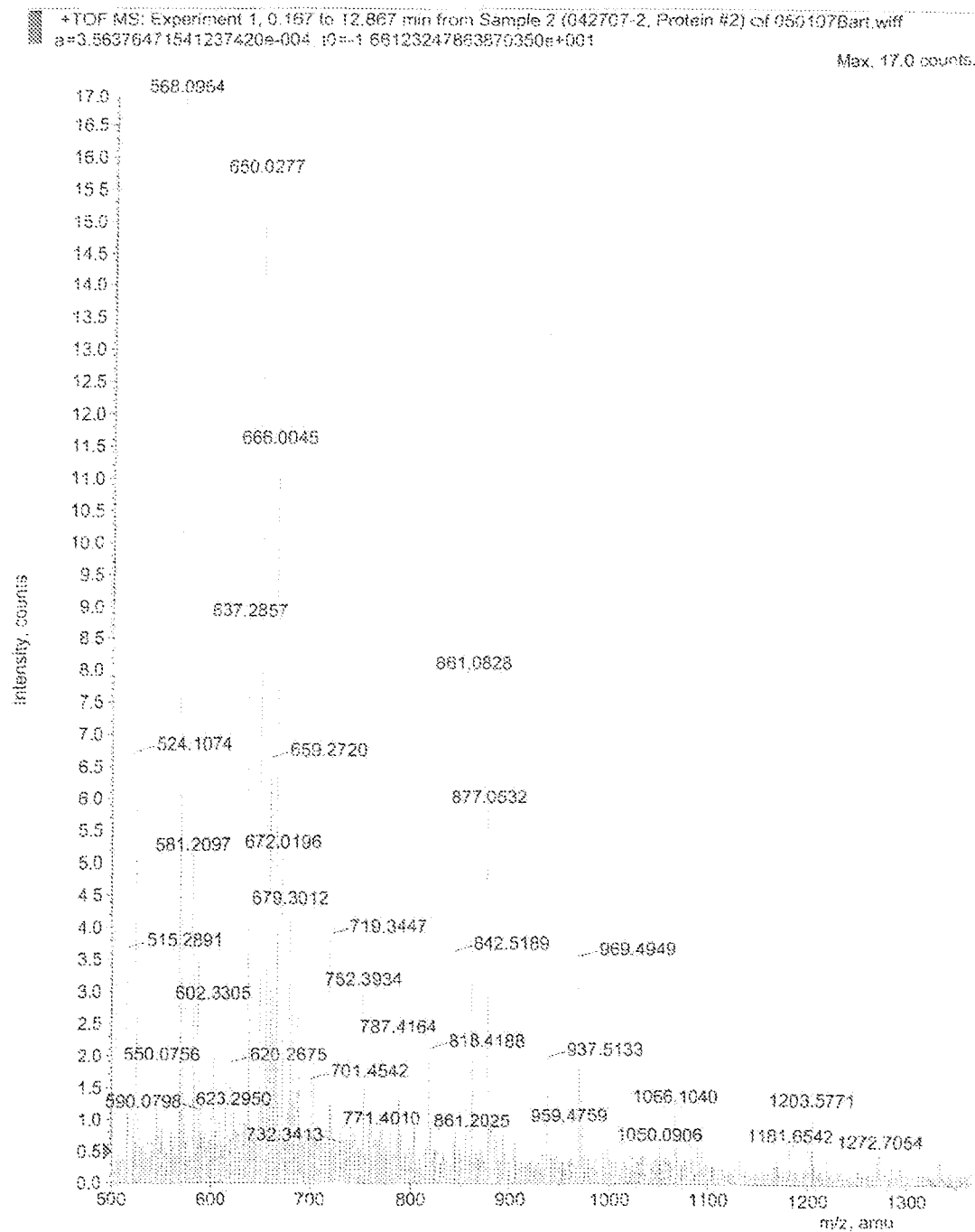
Figure 4D:
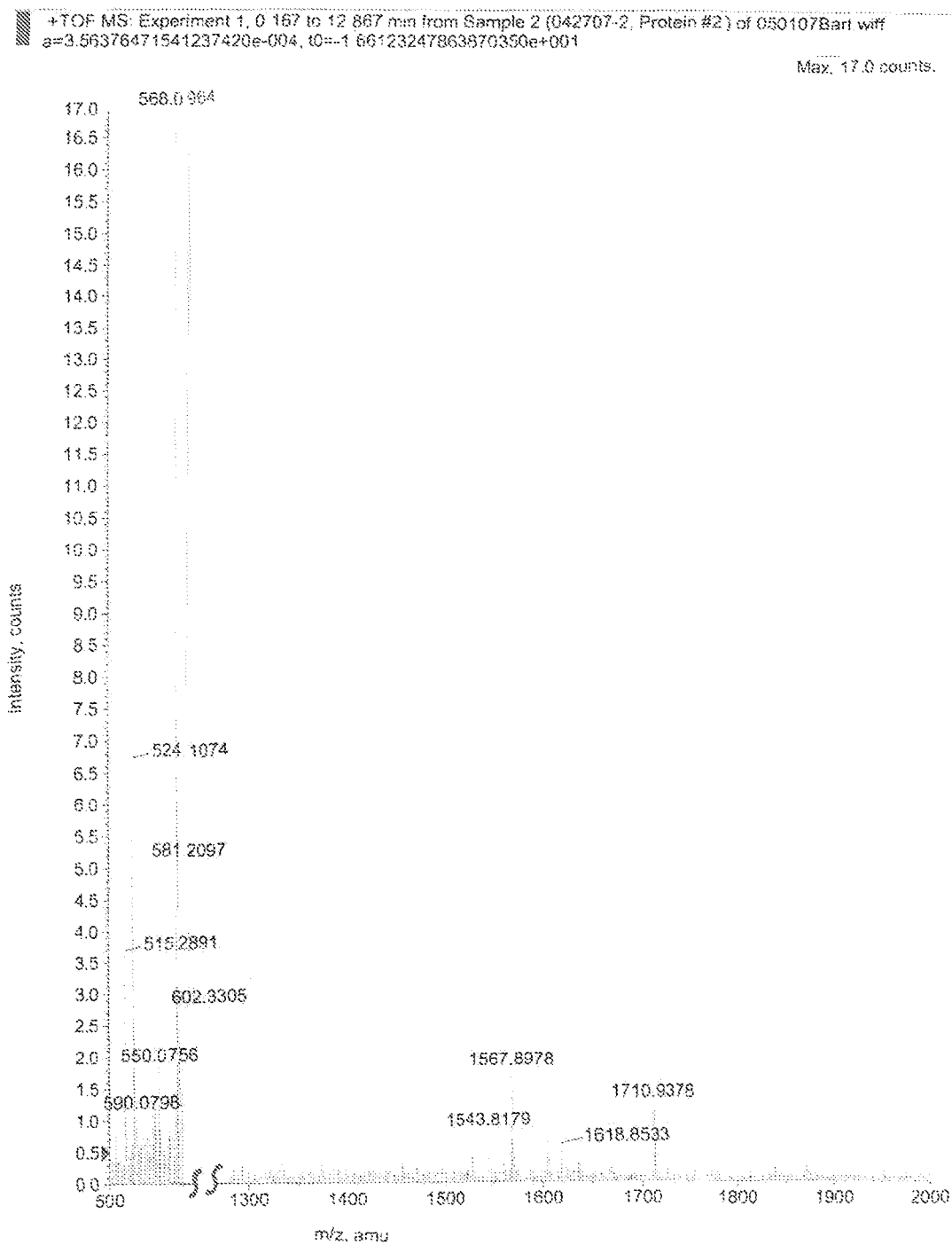
Figure 4E:
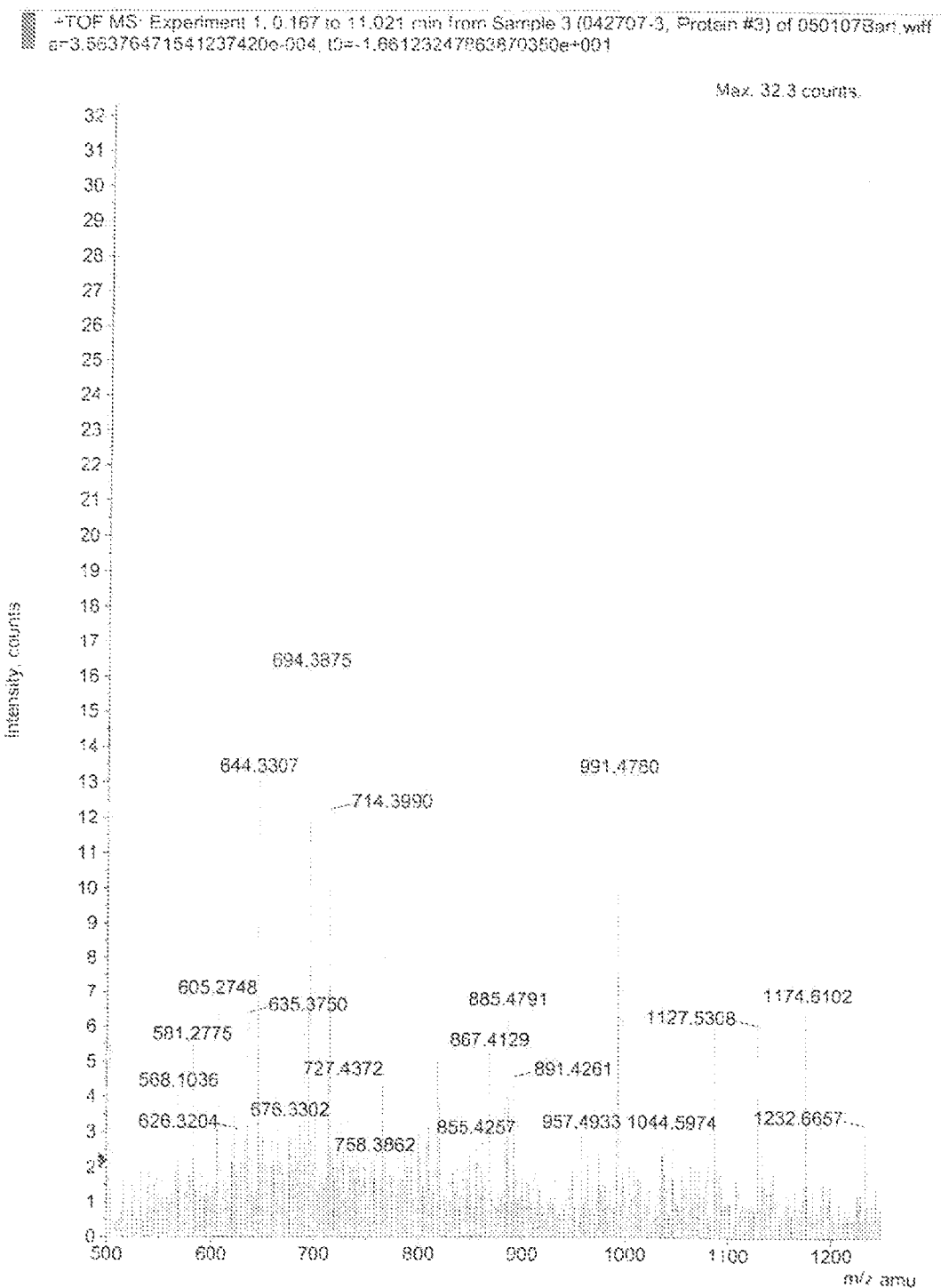
Figure 4F:
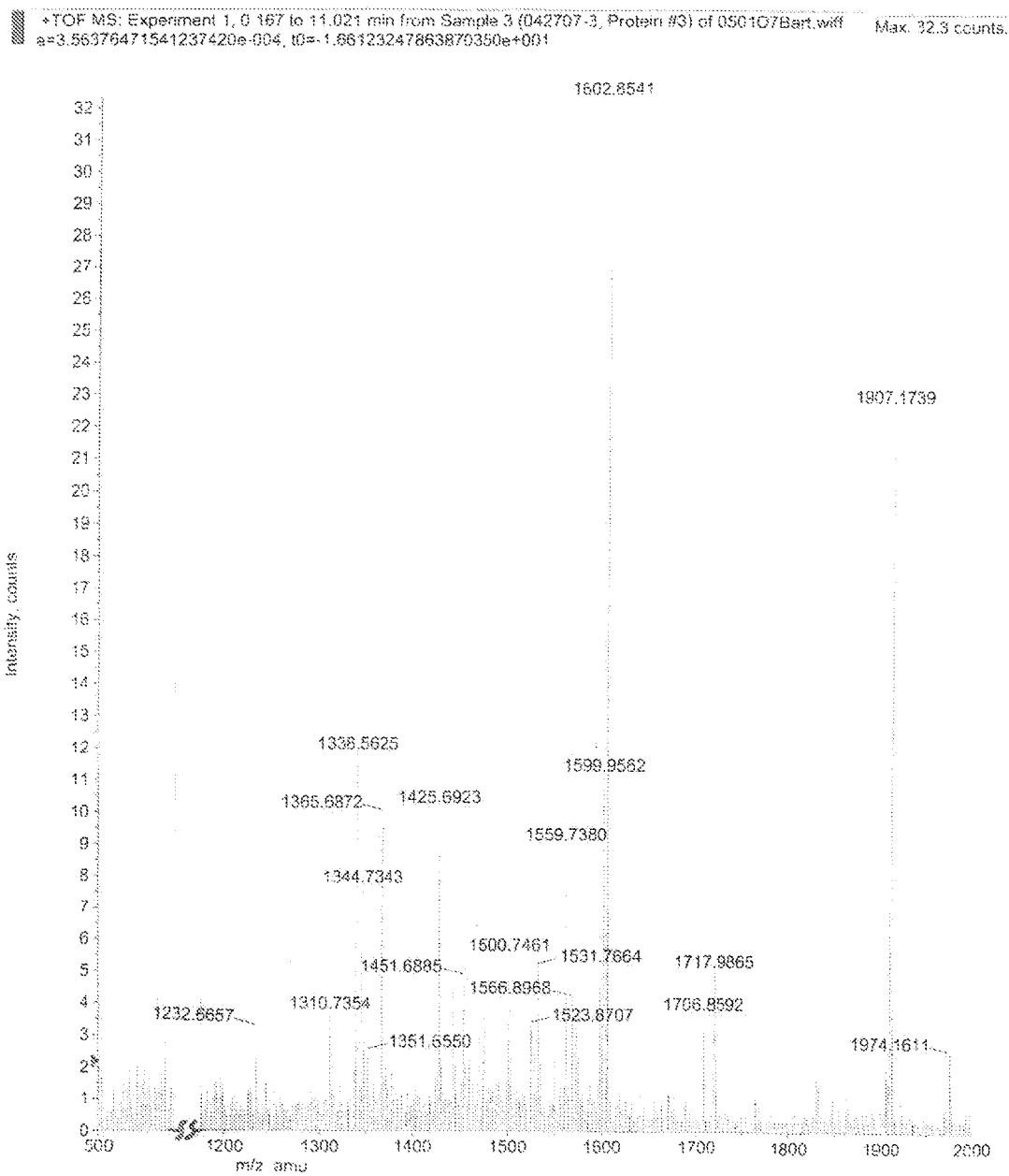
Figure 4G:
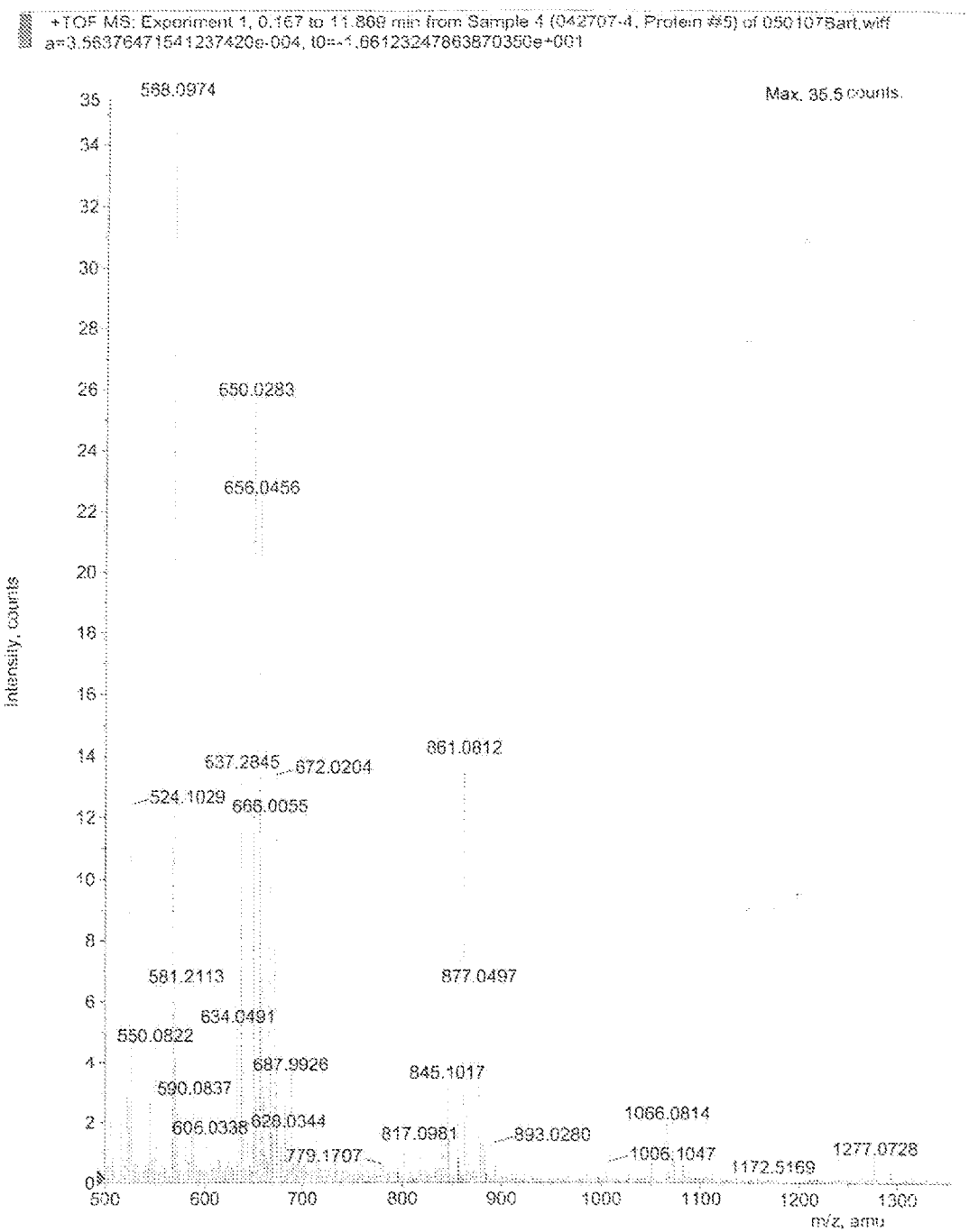
Figure 4H:
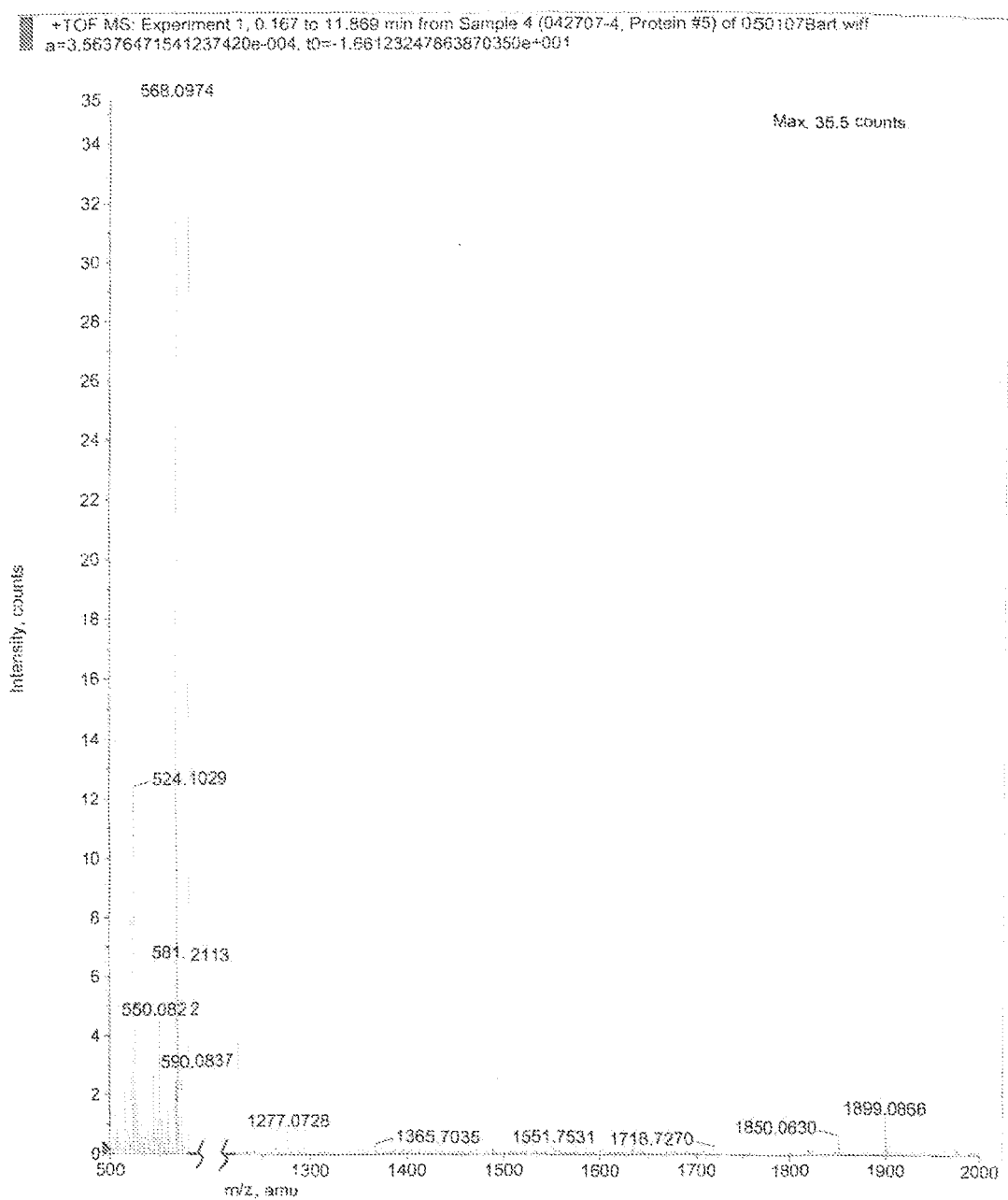

SDS-PAGE was performed using the CRITERION™ gel system with 12.5% acrylamide gels (Bio-Rad Laboratories, Hercules, Calif.). *H. parasuis* cell suspension was run on gels at a 1:3 dilution in PBS. TWEEN® 20 nonionic detergent extract was run undiluted. Gels were stained with GELCODE™ Blue Stain Reagent (Pierce Biotechnology, Inc., Rockford, Ill.), a Coomassie based gel stain. Western blots were run using the PROTEIN DETECTOR™ kit (KPL, Inc., Gaithersburg, Md.). Primary probing was performed using immune fluids generated from the challenged swine. Goat anti-swine-HRP was used as the detection antibody. Visualization was achieved with TMB 1 Component Membrane Peroxidase Substrate (KPL, Inc., Gaithersburg, Md.).

Harvested supernatant from the activated cells isolated from the various tissues of 9 animals were screened against whole serotype 5 *H. parasuis* cells. High concentrations of these supernatants were used for visualization by Western blotting. High and specific concentration of antibody was obtained from the bronchial lymph node of pig 47 (BL47) (FIG. 1). The crude banding pattern present in this Western blot was indicative of proteins present in *H. parasuis* recognized by the challenged animal. BL47 was chosen for further comparative analysis.

Proteins recognized between serotypes were further characterized through a second set of Western blots. Serotypes 5 and 13 were first screened. Serotype 5 showed prominent bands at approximately 28, 33, 45, 56, 63, and 76 kDa. The banding pattern from serotype 13 was similar to serotype 5 and contained prominent bands at 28, 45, 55, 62, and 75 kDa. Testing with BL47 against serotype 4, a serotype not involved in the swine challenges, also generated prominent bands at 28, 34, 41, 47, 57, 62, and 77 kDa. A direct comparison of the three serotypes is shown in FIG. 2. Proteins of approximately 28, 45, 55, 62, and 75 kDa, which appeared to be present in all tested serotypes, were examined further.

Proteins present in multiple serotypes were identified using fluids generated from a sequential challenge. To increase the relative concentrations of membrane-associated proteins in the samples, a culture of serotype 5 was processed via a TWEEN® 20 nonionic detergent extraction process. This method has been previously shown to isolate the outer membranes of bacteria. Performing this procedure produced very few differences in the SDS-PAGE profile from untreated cells (FIG. 3; SDSPAGE), The banding was similar in Western blot, as well, demonstrating that the proteins we initially targeted were present.

The TWEEN® 20 nonionic detergent processed material was used for sequencing. This material contained the cross-reactive proteins and had the majority of cellular debris removed during the course of processing. Thus, this TWEEN® 20 nonionic detergent preparation was run in several adjacent lanes on a PVDF membrane for band cutting and sequencing. (FIG. 3; Blot). Bands selected for sequencing from serotype 5 included those at ~28, ~45, ~56, ~63, and ~76 kDa.

Example 3

Sequencing Results

Samples for sequencing were first run on an SDSPAGE, then transferred to a PVDF membrane. This membrane was stained and bands were excised using a razor blade. Mass spectrometry was performed on gel plugs excised with a razor blade, Transfer buffer was standard Tris/Glycine: buffer with 20% MeOH. The membrane was stained with GELCODE™ Blue Stain Reagent (Pierce Biotechnology, Inc., Rockford, Ill.) and destained with-25% isopropanol in water. The membrane fragments were rinsed copiously with purified, deionized water.

Samples (i.e., ~28, ~45, ~56, ~63, and ~76 kDa bands) were further characterized using mass-spectrometry (FIG. 4A-D) and N-terminal (Edman degradation) sequencing. N-terminal sequencing results provided the partial sequence information, which is shown in Table 2.

TABLE 2

| N-terminal sequencing results. | |
|---|---|
| SPAKGSITEAGIAYPISRA | SEQ ID NO: 6 |
| SEPQATX[1]DAK | SEQ ID NO: 7 |
| MKNLISIAKG | SEQ ID NO: 8 |
| GEIEELALGI | SEQ ID NO: 9 |

TABLE 2-continued

| N-terminal sequencing results. | |
|---|---|
| MEKDVKFGNDARVGMLKGVNXKADA | SEQ ID NO: 10 |
| SEIXELANAITFLSMGVG | SEQ ID NO: 11 |
| GKVPETTVLAXKQEIIX | SEQ ID NO: 12 |
| APAKGSTIEAGIAYPISTAXDDMMS | SEQ ID NO: 13 |
| SPSDKTFKISAIPDYNAAEMTS | SEQ ID NO: 14 |

[1] X represents an undetermined amino acid.

The sequence information for the protein fragments were then BLASTp'd against the *H. influenzae* and *H. ducreyi* in the Swiss-Prot database, Proteins with more than 10 amino acids (aa) or fewer than 3 positions with multiple amino acid possibilities were further analyzed. The results are shown in Table 3.

TABLE 3

Protein Sequencing Results.

| No. | MW (kDa) | Est. MW (kDa) | E-Value | Swiss-Prot ID | Protein Name/Description |
|---|---|---|---|---|---|
| 1 | 28 | 22 | 0.76 | Q4QM69 | Monofunctional biosynthetic peptidoglycan transglyosylase |
| 2 | 28 | 34 | 2.5 | Q4QK43 | tRNA pseudouridine synthase B |
| 3 | 28 | 32 | 3.4 | Q4QJL4 | Enoyl-[acyl-carrier-protein] reductase |
| 4 | 28 | 68 | 8 | Q4QLZ8 | Glutathione-regulated potassium-efflux system |
| 5 | 56 | 60 | 8.00E−08 | Q4QM48 | Heme-binding protein A |
| 6[a] | 56 | 58 | 0.041 | Q7VL18 | Putative ABC transporter periplasmic binding protein |
| 7 | 63 | 61 | 0.33 | Q4QLH0 | Periplasmic oligopeptide-binding protein |
| 8 | 63 | 28 | 1.9 | Q4QNT7 | TonB (iron transporter) |
| 9 | 76 | 68 | 4.00E−09 | Q4QJW4 | Chaperone protein dnaK (HSP70) |
| 10 | 76 | 24 | 0.59 | Q4QP42 | Putative N-acetylmannosamine-6-phosphate 2-epimerase |
| 11 | 76 | 17 | 1.1 | Q4QMR6 | Phosphopantetheine adenylyltransferase |
| 12 | 76 | 74 | 2 | Q4QJR2 | HMW1C, putative glycosyltransferase involved in glycosylation of HMW1A and HMW2A |

[a] = Protein sequence hit against *H. ducreyi*. All other sequences obtained through comparison to *H. influenzae*.

Table 3 includes at least two proteins that appear likely to be exposed on the cell's surface (proteins 6 and 7) and at least one that appears to be able to bind iron (protein 5).

Example 4

PCR and Cloning

Proteins 5 and 6 shown in Table 3 were immunogenic as they were both recognized by the swine immune fluids. These proteins have been associated with iron acquisition. ABC-type transporters have a wide variety of reported functions and have been connected with iron uptake in Cyanobacteria. The heme-binding protein is vital for *H. influenzae*'s survival in the blood stream as it harvests iron bound to heme groups. Further, the heme-binding protein is highly conserved within the genus.

Using published *H. influenzae* and *H. ducreyi* genome information, PCR primers were designed to amplify the two selected proteins (i.e proteins 5 and 6) from an *H. parasuis* chromosomal prep. The PCR primers used are shown in Table 4.

TABLE 4

PCR primers.

| Name | Sequence (5' to 3') | $T_M$ |
|---|---|---|
| Protein 5 | | |
| FHpsHemeBam (forward) | TATAGGATCCATGCTTATGAAACTAAAAGCA ACATTAACT SEQ ID NO: 15 | 60° C |
| RHpsHemeXho (reverse) | TATACTCGAGTTATTTACCATCAACACTCAC ACCATAAAA SEQ ID NO: 16 | 61° C |
| Protein 6 | | |
| FHpsABCBam (forward) | TATAGGATCCATGACTTCTCATTTTGAATAC AATCAATCT SEQ ID NO: 17 | 60° C |
| RHpsABCXho (reverse) | TATACTCGAGTTATGTACGACCTACACCAAG GAAAGACAA SEQ ID NO: 18 | 64° C |

For amplification of a nucleotide sequence corresponding to protein 5, PCR was performed using the primers shown in Table 4 and PPO Turbo polymerase, and *H. parasuis* chromosomal preparation as template. Two solid bands were seen in the heme reaction (~1.8 kb and ~800 bp) and the band corresponding to the ~1.8 kb amplification product was gel purified.

For amplification of a nucleotide sequence corresponding to protein 6, PCR was performed using the primers shown in Table 4 and Pfu Turbo polymerase and *H. Parasuis* chromosomal preparation as template. A doublet was seen in this reaction (~1.5 kb and ~1.3 kb) and the top band (i.e., ~1.5 kb) of the doublet was gel purified using a gel elution kit.

The gel purified fluids containing the amplified products were A-tailed and ligated to pGEM®-T vector. This ligation was transformed into TOP10 competent cells (Invitrogen Corporation, Carlsbad, Calif.). Transformants were picked and grown at 37° C. over night. Inserts were subsequently confirmed and subcloned into the pTRCHis-A expression vector (Invitrogen Corporation, Carlsbad, Calif.) expression of recombinant proteins containing N terminal 6×His Tags.

What is claimed is:

1. A method for indicating presence of a cross-reactive antigenic determinant on two or more molecules, the method comprising the steps of:

Obtaining at least one antibody from an animal exposed to a first immunological challenge comprising a first antigenic determinant followed by a second immunological challenge comprising a second antigenic determinant, wherein the first antigenic determinant is expressed by a first *H. parasuis* microorganism and the second antigenic determinant is expressed by a second *H. parasuis* microorganism, and wherein the first and second *H. parasuis* microorganisms are characterized as being different serotypes;

contacting the at least one antibody with a first antigenic determinant and detecting binding; and contacting the at least one antibody with a second antigenic determinant and detecting binding, wherein binding of the at least one antibody to both the first and the second antigenic determinant is indicative of antibody cross-reactivity between antigenic determinants of two different *H. parasuis* serotypes.

2. The method of claim 1, wherein the first *H. parasuis* microorganism is serotype 5, and wherein the second *H. parasuis* microorganism is serotype 13.

3. The method of claim 1, wherein at least one of the first and the second antigenic determinants is present in a heme-binding protein.

4. The method of claim 1, wherein the first and the second antigenic determinants comprise an amino acid sequence selected from the group consisting of:

```
                                   (SEQ ID NO: 1)
ELANAI;

(SEQ ID NO: 2)
TVLAEKQEII;

(SEQ ID NO: 3)
APAKGSTIEAGIAYPIST (SEQ ID NO: 4)
MKNLISI;
and (SEQ ID NO: 5)
SPSDKTFKISAIPDYNAAEMT.
```

5. The method of claim 1, wherein the animal is a porcine.

* * * * *

SEQUENCE LISTING

<160> NUMBER OF SEQ ID NOS: 18

<210> SEQ ID NO 1
<211> LENGTH: 6
<212> TYPE: PRT
<213> ORGANISM: Haemophilus parasuis

<400> SEQUENCE: 1

Glu Leu Ala Asn Ala Ile
1               5

<210> SEQ ID NO 2
<211> LENGTH: 10
<212> TYPE: PRT
<213> ORGANISM: Haemophilus parasuis

<400> SEQUENCE: 2

Thr Val Leu Ala Glu Lys Gln Glu Ile Ile
1               5                   10

<210> SEQ ID NO 3
<211> LENGTH: 18
<212> TYPE: PRT
<213> ORGANISM: Haemophilus parasuis

<400> SEQUENCE: 3

Ala Pro Ala Lys Gly Ser Thr Ile Glu Ala Gly Ile Ala Tyr Pro Ile
1               5                   10                  15

Ser Thr

<210> SEQ ID NO 4
<211> LENGTH: 7
<212> TYPE: PRT
<213> ORGANISM: Haemophilus parasuis

<400> SEQUENCE: 4

Met Lys Asn Leu Ile Ser Ile
1               5

<210> SEQ ID NO 5
<211> LENGTH: 21
<212> TYPE: PRT
<213> ORGANISM: Haemophilus parasuis -continued

```
<400> SEQUENCE: 5

Ser Pro Ser Asp Lys Thr Phe Lys Ile Ser Ala Ile Pro Asp Tyr Asn
1               5                   10                  15

Ala Ala Glu Met Thr
            20

<210> SEQ ID NO 6
<211> LENGTH: 19
<212> TYPE: PRT
<213> ORGANISM: Haemophilus parasuis

<400> SEQUENCE: 6

Ser Pro Ala Lys Gly Ser Thr Ile Glu Ala Gly Ile Ala Tyr Pro Ile
1               5                   10                  15

Ser Arg Ala

<210> SEQ ID NO 7
<211> LENGTH: 10
<212> TYPE: PRT
<213> ORGANISM: Haemophilus parasuis
<220> FEATURE:
<221> NAME/KEY: misc_feature
<222> LOCATION: (7)..(7)
<223> OTHER INFORMATION: Xaa can be any naturally occurring amino acid

<400> SEQUENCE: 7

Ser Glu Pro Gln Ala Thr Xaa Asp Ala Lys
1               5                   10

<210> SEQ ID NO 8
<211> LENGTH: 10
<212> TYPE: PRT
<213> ORGANISM: Haemophilus parasuis

<400> SEQUENCE: 8

Met Lys Asn Leu Ile Ser Ile Ala Lys Gly
1               5                   10

<210> SEQ ID NO 9
<211> LENGTH: 10
<212> TYPE: PRT
<213> ORGANISM: Haemophilus parasuis

<400> SEQUENCE: 9

Gly Glu Ile Glu Glu Leu Ala Leu Gly Ile
1               5                   10

<210> SEQ ID NO 10
<211> LENGTH: 25
<212> TYPE: PRT
<213> ORGANISM: Haemophilus parasuis
<220> FEATURE:
<221> NAME/KEY: misc_feature
<222> LOCATION: (21)..(21)
<223> OTHER INFORMATION: Xaa can be any naturally occurring amino acid

<400> SEQUENCE: 10

Met Glu Lys Asp Val Lys Phe Gly Asn Asp Ala Arg Val Gly Met Leu
1               5                   10                  15

Lys Gly Val Asn Xaa Lys Ala Asp Ala
            20                  25

<210> SEQ ID NO 11
```

```
<211> LENGTH: 18
<212> TYPE: PRT
<213> ORGANISM: Haemophilus parasuis
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

Ser Glu Ile Xaa Glu Leu Ala Asn Ala Ile Thr Phe Leu Ser Met Gly
1               5                   10                  15

Val Gly

<210> SEQ ID NO 12
<211> LENGTH: 17
<212> TYPE: PRT
<213> ORGANISM: Haemophilus parasuis
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (17)..(17)
<223> OTHER INFORMATION: Xaa can be any naturally occurring amino acid

<400> SEQUENCE: 12

Gly Lys Val Pro Glu Thr Thr Val Leu Ala Xaa Lys Gln Glu Ile Ile
1               5                   10                  15

Xaa

<210> SEQ ID NO 13
<211> LENGTH: 25
<212> TYPE: PRT
<213> ORGANISM: Haemophilus parasuis
<220> FEATURE:
<221> NAME/KEY: misc_feature
<222> LOCATION: (20)..(20)
<223> OTHER INFORMATION: Xaa can be any naturally occurring amino acid

<400> SEQUENCE: 13

Ala Pro Ala Lys Gly Ser Thr Ile Glu Ala Gly Ile Ala Tyr Pro Ile
1               5                   10                  15

Ser Thr Ala Xaa Asp Asp Met Met Ser
            20                  25

<210> SEQ ID NO 14
<211> LENGTH: 22
<212> TYPE: PRT
<213> ORGANISM: Haemophilus parasuis

<400> SEQUENCE: 14

Ser Pro Ser Asp Lys Thr Phe Lys Ile Ser Ala Ile Pro Asp Tyr Asn
1               5                   10                  15

Ala Ala Glu Met Thr Ser
            20

<210> SEQ ID NO 15
<211> LENGTH: 40
<212> TYPE: DNA
<213> ORGANISM: Haemophilus parasuis

<400> SEQUENCE: 15
tataggatcc atgcttatga aactaaaagc aacattaact                            40
```

-continued

```
<210> SEQ ID NO 16
<211> LENGTH: 40
<212> TYPE: DNA
<213> ORGANISM: Haemophilus parasuis

<400> SEQUENCE: 16
tatactcgag ttatttacca tcaacactca caccataaaa                        40

<210> SEQ ID NO 17
<211> LENGTH: 40
<212> TYPE: DNA
<213> ORGANISM: Haemophilus parasuis

<400> SEQUENCE: 17
tataggatcc atgacttctc attttgaata caatcaatct                        40

<210> SEQ ID NO 18
<211> LENGTH: 40
<212> TYPE: DNA
<213> ORGANISM: Haemophilus parasuis

<400> SEQUENCE: 18
tatactcgag ttatgtacga cctacaccaa ggaaagacaa                        40
```